US008734851B2

(12) United States Patent
Lynn et al.

(10) Patent No.: US 8,734,851 B2
(45) Date of Patent: May 27, 2014

(54) LOCALIZED DELIVERY OF NUCLEIC ACID BY POLYELECTROLYTE ASSEMBLIES

(75) Inventors: David M. Lynn, Middleton, WI (US); Jingtao Zhang, Madison, WI (US); Christopher M. Jewell, Madison, WI (US); Nathaniel J. Fredin, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 353 days.

(21) Appl. No.: 11/414,818

(22) Filed: May 1, 2006

(65) Prior Publication Data

US 2006/0251701 A1  Nov. 9, 2006

Related U.S. Application Data

(60) Provisional application No. 60/676,410, filed on Apr. 29, 2005.

(51) Int. Cl.
| | | |
|---|---|---|
| A61K 9/16 | (2006.01) | |
| A61K 9/14 | (2006.01) | |
| A61K 47/44 | (2006.01) | |
| C12Q 1/68 | (2006.01) | |
| C12N 15/00 | (2006.01) | |
| C12N 15/88 | (2006.01) | |
| C12N 15/87 | (2006.01) | |

(52) U.S. Cl.
USPC ........ 424/497; 424/486; 424/280.1; 435/455; 435/458; 435/465

(58) Field of Classification Search
USPC ........... 424/497, 486, 281.1; 435/6, 455, 458, 435/465
See application file for complete search history.

(56) References Cited

U.S. PATENT DOCUMENTS

| 6,274,322 | B1 | 8/2001 | Curiel et al. | |
|---|---|---|---|---|
| 6,312,727 | B1 | 11/2001 | Schacht et al. | |
| 6,353,055 | B1 | 3/2002 | Kabanov et al. | |
| 6,365,173 | B1 | 4/2002 | Domb et al. | |
| 6,383,811 | B2 | 5/2002 | Wolf et al. | |
| 6,395,253 | B2 | 5/2002 | Levy et al. | |
| 6,544,790 | B1 | 4/2003 | Sabatini | |
| 6,743,521 | B2 * | 6/2004 | Hubbell et al. | 428/500 |
| 6,998,115 | B2 | 2/2006 | Langer et al. | |
| 7,112,361 | B2 | 9/2006 | Lynn et al. | |
| 2001/0006817 | A1 | 7/2001 | Pack et al. | |
| 2002/0012652 | A1 | 1/2002 | Levy et al. | |
| 2002/0131951 | A1 | 9/2002 | Langer et al. | |
| 2002/0146459 | A1 | 10/2002 | Levy et al. | |
| 2002/0164315 | A1 | 11/2002 | Wolf et al. | |
| 2003/0026840 | A1 | 2/2003 | Plank et al. | |
| 2003/0073619 | A1 | 4/2003 | Mahato et al. | |
| 2005/0027064 | A1 | 2/2005 | Lynn et al. | |
| 2005/0265956 | A1 | 12/2005 | Liu et al. | |
| 2005/0282925 | A1 * | 12/2005 | Schlenoff et al. | 523/106 |
| 2006/0093607 | A1 * | 5/2006 | Gerber et al. | 424/145.1 |
| 2007/0020469 | A1 | 1/2007 | Wood et al. | |

FOREIGN PATENT DOCUMENTS

| WO | WO 2004/009665 | 1/2004 |
|---|---|---|
| WO | WO 2004/009666 | 1/2004 |

OTHER PUBLICATIONS

Vazquez et al., Construction of hydrolytically-degradable thin films via layer-by-layer deposition of degradable polyelectrolytes.J Am Chem Soc. Nov. 27, 2002;124(47):13992-3.*
Klugherz BD, et al., Gene delivery from a DNA controlled-release stent in porcine coronary arteries. Nat Biotechnol. Nov. 2000;18(11):1181-4.*
Klugherz et al., Human Gene Therapy Feb. 2002, 13(3): 443-454. Gene Delivery to Pig Coronary Arteries from Stents Carrying Antibody-Tethered Adenovirus.*
Fishbein et al., PNAS 2006 159-164 Bisphosphonate-mediated gene vector delivery from the metal surfaces of stents.*
Perlstein et al., Gene Therapy (2003) 10, 1420-1428 DNA delivery from an intravascular stent with a denatured collagen-polylactic-polyglycolic acid-controlled release coating: mechanisms of enhanced transfection.*
Blacklock, J. et al. "disassembly of layer-by-layer films of plasmid DNA and reducible TAT polypeptide"; (2007) Biomaterials28:117.
Chen, J. et al. "Tunable Film Degradation and Sustained Release of Plasmid DNA from Cleavable Polycation/Plasmid DNA Multilayers under Reductive Conditions"; (2007) Small3:636.
Decher, G. "Fuzzy Nanoassemblies: Toward Layered Polymeric Multicomposites"; (1997) Science277:1232.
De Geest, B.G. et al."Intracellularly Degradable Polyelectrolyte Microcapsules";(2006) Adv. Mater.18:1005.
Fredin, N.J. et al. "Surface Analysis of Erodible Multilayered Polyelectrolyte Films: Nanometer-Scale Structure and Erosion Profiles"; (2005) Langmuir21:5803.
Fredin, N.J. et al. "Nanometer-Scale Decomposition of Ultrathin Multilayered Polyelectrolyte Films", (2007) Langmuir23:2273.
Funhoff, A.M. et al. "Poly Side-chain degradation as a Tool to Control the Destabilization of Polyplexes"; (2004) Pharm. Res. 21:170
Hammond, P.T. "Form and Function in Multilayer Assembly: New Applications at the Nanoscale"; (2004) Adv. Mater. 16:1271.
Heilmann, S.M. et al. "Highlight—Chemistry and Technology of 2-Alkenyl Azlactones"; (2001) J. Polym. Sci. Poly. Chem. 39:3655.
Jessel, N. et al. "Multiple and time-scheduled in situ DNA delivery mediated by β- cyclodextrin embedded in a polyelectrolyte multilayer"; (2006) Proc. Natl. Acad. Sci. USA103:8618.
Jewell, C.M. et al."Release of Plasmid DNA from Intravascular Stents Coated with Ultrathin Multilayered Polyelectrolyte Films"; (2006) Biomacromolecules7:2483.

(Continued)

Primary Examiner — Maria Leavitt
(74) Attorney, Agent, or Firm — Lathrop & Gage LLP

(57) ABSTRACT

The present invention provides implantable medical devices coated with polyelectrolyte assemblies that are fabricated by layer-by-layer deposition of nucleic acid and polycation. Such devices facilitate the local delivery of a nucleic acid contained in the polyelectrolyte assembly into a cell or tissue at an implantation site. Also provided are methods of fabricating and using implantable medical devices according to the invention.

21 Claims, 6 Drawing Sheets

(56) References Cited

OTHER PUBLICATIONS

Jewell, C.M. et al. "Multilayered polyelectrolyte films promote the direct and localized delivery of DNA cells"; (2005) *J.Control. Release*106:214.

Klugherz, B.D. et al. "Gene delivery from a DNA controlled release stent in porcine coronary arteries"; (2000) *Nat. Biotechnol.* 18:1181.

Liu, X. et al. "Charge-Shifting Cationic Polymers that Promote Self-Assembly and Self-Disassembly with DNA"; (2005) *Macromolecules*38:7907.

Luten, J. et al. "Methacrylamide Polymers with Hydrolysis-Sensitive Cationic Side Groups as Degradable Gene Carriers"; (2006) *Bioconjugate Chem.* 17:1077.

Lvov, Y. et al. "Assembly of Thin Films by Means of Successive Deposition of Alternate Layers of DNA and Poly(allylamine)";(1993) *Macromolecules*26:5396.

Lynn, D.M. et al. "Layers of opportunity: nanostructured polymer assemblies for the delivery of macromolecular therapeutics"; (2006) *Soft Matter*2:269.

Ren, K.F. et al. "Construction and enzymatic degradation of multilayered poly-L-lysine/DNA films"; (2006) *Biomaterials*27:1152.

Ren, K.F. et al. "Tunable DNA Release from Cross-Linked Ultrathin DNA/PLL Multilayered Films"; (2006) *Bioconjugate Chem.* 17:77.

Segura, T. et al. Surf-tethered DNA Complexes for Enhanced Gene Delivery; (2002) *Bioconjugate Chem.* 13:621.

Shea, L.D. et al. "DNA delivery from polymer matrices for tissue engineering"; (1999) *Nat. Biotechnol.* 17:551.

Veron, L. et al. "New Hydrolyzable pH-Responsive Cationic Polymers for Gene Delivery: A Preliminary Study"; (2004) *Macromol. Biosci.* 4:431.

Wu, R.Z. et al. "Cell-biological applications of transfected-cell microarrays"; (2002) *Trends Cell Biol.* 12:485.

Zhang, J. et al. "Multilayered Thin Films that Sustain the Release of Functional DNA under Physiological Conditdions"; (2004) *Langmuir*20:8015.

Ziauddin, J. et al. "Microarrays of cells expressing defined cDNAs"; (2001) *Nature*411:107.

Barrera, et al. (1993) *J. Am. Chem. Soc.* 115:11010-11011.

Berg, C. et al. "Controlled Drug Release from Porous polyelectrolyte Multilayers";(2006) *Biomacromolecules*7:357-364.

Cotten et al. (1993) *Methods Enzymol*217:618.

Fishbein, I. et al., "Site specific gene delivery in the cardiovascular system"; (2005) *J. Control Release*109:37-48.

Fishbein, I. et al., "Bisphosphonate-mediated gene vector delivery from the metal surfaces of stents"; (2006) *Proc. Natl. Acad. Sci. USA*103:159-164.

Goeddel, (1990) *Methods Enzymol*185:3-7.

Groth, T. et al., "Layer-by-Layer Deposition of Polyelectrolytes—A Versatile tool for the In Vivo Repair of Blood Vessels"; (2004)*Agnew Chem. Int. Ed. Engl.*43:926-928.

Jewell et al., "Multilayered polyelectrolyte assemblies as platforms for the delivery of DNA and other nucleic acid-based therapeutics"; (2008) *Advanced Drug Delivery Reviews*60:979-999.

Jewell et al., "Surface-mediated delivery of DNA: Cationic polymers take charge"; (2008) *Current Opinion in Colloid & Interface Science*13:395-402.

Klugherz, B.D. et al., "Gene delivery from a DNA controlled-release stent in porcine coronary arteries"; (2000) *Nat. Biotechnol.* 18:1181-1184.

Kwon et al. (1989) *Macromolecules*22:3250-3255.

Lim et al. (1999) *J. Am. Chem. Soc.* 121:5633-5639.

Lim, Y. et al. "Development of a Safe Gene Delivery System using Biodegradable Polymer, Poly[alpha-(4-aminobutyl)-L-glycolic acid]"; (2000) *J. Am. Chem. Soc.* 122:6524-6525.

Little, S.R. et al. "Poly-beta amino ester-containing microparticles enhance the activity of nonviral genetic vaccines"; (2004)*Proc. Natl. Acad. Sci. USA*101:9534-9539.

Luo, D. et al., "Synthetic DNA delivery systems"; (2000) *Nat. Biotechnol.* 18:33-37.

Lynn, D.M. et al., "Degradable Poly(.beta.-Amino Esters): Synthesis, Characterization, and Self-Assembly with Plasmid DNA"; (2000) *J. Am. Chem. Soc.* 122:10761-10768.

Lynn et al., "Peeling Back the Layers: Controlled Erosion and Triggered Disassembly of Multilayered Polyelectrolyte Thin Films"; (2007) *Advanced Materials*19:4118-4130.

Pack, D.W. et al. "Design and development of polymers for gene delivery"; (2005) *Nature Reviews Drug Discovery*4:581-593.

Perlstein, I. et al., "DNA delivery from an intravascular stent with a denatured collagen-polylactic-polyglycolic acid-controlled release coating: mechanisms of enhanced transfection"; (2003) *Gene Therapy*10:1420-1428.

Peterson, H. et al., "Poly(ethyleneimine-co-L-lactamide-co-succinamide): A Biodegradable Polyethyleneimine Derivative with an Advantageous pH-Dependent Hydrolytic Degradation for Gene Delivery"; (2002) *Bioconjugate Chem.* 13:812-821.

Peyratout, C.S. et al., "Tailor-made polyelectrolyte microcapsules: from multilayers to smart containers"; (2004) *Agnew Chem.Int. Ed. Engl.* 43:3762-3783.

Putnam, D. et al., "Poly(4-hydroxy-1-proline ester): Low-Temperature Polycondensation and Plasmid DNA Complexation"; (1999) *Macromolecules*32:3658-3662.

Schuler, C. et al., "Decomposable hollow biopolymer-based capsules"; (2001) *Biomacromolecules*2:921-926.

Sukhishsvili, A., "Responsive polymer films and capsules via layer-by-layer assembly"; (2005) *Current Opinion in Colloid & Interface Science*10:37-44.

Takahashi, A. et al., "Transgene delivery of plasmid DNA to smooth muscle cells and macrophages from a biostable polymer-coated stent" (2003) *Gene Therapy*10:1471-1478.

Takahashi et al., "Delivery of Large Biopharmaceuticals from Cardiovascular Stents: A Review"; (2007) *Biomacromolecules*, 8(11):3281-3293.

Walter, D.H. et al., "Local gene transfer of phVEGF-2 plasmid by gene-eluting stents: an alternative strategy for inhibition of restenosis"; (2004) *Circulation*110:36-45.

Wang, J. et al., "A Novel Biodegradable Gene Carrier Based on Polyphosphoester"; (2001) *J. Am. Chem. Soc.* 123:9480-9481.

Zhang, J. et al. "Erosion of Multilayered Films Fabricated from Degradable Polyamines: Characterization and Evidence in Support of a Mechanism that Involves Polymer Hydrolysis"; (2006) *J. of Polymer Science—Part A: Polymer Chemistry*44: In Press.

Zhang, N.J. et al., "Structure/Property Relationships in Erodible Multilayered Films: Influence of Polycation Structure on Erosion profiles and the Release of Anionic Polyelectrolytes"; (2006) *Langmuir*22:239-245.

Zhou et al (1990) *Macromolelcules*23:3399-3406.

\* cited by examiner

A)   B)

A)

B)

C)

LOCALIZED DELIVERY OF NUCLEIC ACID BY POLYELECTROLYTE ASSEMBLIES

CROSS-REFERENCE TO RELATED APPLICATIONS

This application claims the benefit of U.S. Provisional application 60/676,410, filed Apr. 29, 2005, incorporated herein by reference in its entirety.

STATEMENT REGARDING FEDERALLY SPONSORED RESEARCH

This invention was made with government support under EB002746 awarded by the National Institutes of Health. The government has certain rights in the invention.

FIELD OF THE INVENTION

This invention relates generally to the field of nucleic acid delivery into cells (i.e., transfection). More particularly, the present invention relates to the localized delivery of nucleic acids to cells using polyelectrolyte assemblies that are fabricated by layer-by-layer deposition of nucleic acid and polycation.

BACKGROUND OF THE INVENTION

Thin films and coatings that sustain the release of DNA from surfaces are playing an important role in the development of localized approaches to gene therapy. For example, polymer-coated intravascular stents have been used to localize the delivery of DNA to the vascular wall and could lead to innovative gene-based treatments for vascular diseases or related conditions. Likewise, plasmid-eluting polymer matrices have been applied to the localized delivery of DNA to cells in the context of tissue engineering. The integration of design elements and new chemical functionalities that provide for the erosion of polyelectrolyte films under physiological conditions have been described for use in certain therapeutic areas. Several groups have reported the enzymatic degradation of multilayered films fabricated from naturally occurring polyelectrolytes such as chitosan/dextran sulfate, DNA, or hyaluronic acid and chitosan.

Intravascular stents have previously demonstrated potential as platforms for the localized delivery of DNA. This past work has focused largely on the encapsulation of plasmid DNA in thin films of degradable polymer (I. Fishbein, et al., Site specific gene delivery in the cardiovascular system. *J Control Release* 2005, 109, 37-48; B. D. Klugherz, et al., Gene delivery from a DNA controlled-release stent in porcine coronary arteries. *Nat Biotechnol* 2000, 18, 1181-4; I. Perlstein, et al., DNA delivery from an intravascular stent with a denatured collagen-polylactic-polyglycolic acid-controlled release coating: mechanisms of enhanced transfection. *Gene Ther* 2003, 10, 1420-8; A. Takahashi, et al., Transgene delivery of plasmid DNA to smooth muscle cells and macrophages from a biostable polymer-coated stent. *Gene Ther* 2003, 10, 1471-8; D. H. Walter, et al., Local gene transfer of phVEGF-2 plasmid by gene-eluting stents: an alternative strategy for inhibition of restenosis. *Circulation* 2004, 110, 36-45.) or the tethering of viruses to collagen-coated stents (B. D. Klugherz, et al., Gene delivery to pig coronary arteries from stents carrying antibody-tethered adenovirus. *Hum Gene Ther* 2002, 13, 443-54) or bare metal stents (I. Fishbein, et al., Bisphosphonate-mediated gene vector delivery from the metal surfaces of stents. *Proc Natl Acad Sci USA* 2006, 103, 159-164).

In the long term, methods for non-viral gene delivery have the potential to be safer than methods based on the use of viruses. However, past studies on stent-mediated delivery of plasmid DNA have made use of relatively thick (micrometer-scale) films using polymers that have been observed to lead to inflammatory responses in vivo. In addition, conventional methods for the bulk encapsulation of DNA involve the use of organic solvents, and these methods provide limited control over DNA loading and the spatial distribution of encapsulated DNA. The development of ultrathin films that combine the ability to localize DNA at a surface with the ability to control release profiles and promote subsequent internalization would constitute a significant advance and make possible new approaches to localized gene delivery.

Although various degradable polymer matrices have been described that are capable of sustaining the release of encapsulated DNA, general methods for the direct, localized, and sequential delivery of nucleic acid from thin films and surfaces do not yet exist. Such direct transfection materials and methods would be particularly advantageous in medical applications including, but not limited to, localized gene therapy, the growth or regeneration of complex tissues and other therapeutic uses such as inhibiting and/or ameliorating the inflammation that accompanies the implantation of medical devices such as vascular stents, prosthesis and the like.

SUMMARY OF THE INVENTION

In a first aspect, the invention provides an implantable medical device capable of localized delivery of nucleic acid to a cell. Such an implantable medical device includes a polyelectrolyte assembly coating a surface of the medical device. This polyelectrolyte assembly includes at least one nucleic acid/polycation bilayer fabricated by layer-by-layer deposition of nucleic acid and polycation.

A wide range of polycations, both degradable and non-degradable, are useful in fabricating a device according to the invention. Particularly useful polycations are hydrolytically or enzymatically degradable polycations including, but not limited to, poly(beta-amino ester)s, poly(4-hydroxy-L-proline ester), poly[alpha-(4-aminobutyl)-L-glycolic acid], and combinations thereof.

In certain embodiments, the polyelectrolyte assembly includes multiple nucleic acid/polycation bilayers, preferably more than two bilayers. In embodiments containing multiple bilayers, these bilayers may alternatively differ from each other in their specific composition of nucleic acid and/or polycation. Accordingly, respective bilayers may incorporate varied nucleic acids that differ by nucleic acid sequence and those nucleic acids may, in alternative embodiments, be incorporated into one or more expression vectors. Similarly, bilayers may differ from each other in their specific polycation makeup as in certain embodiments where differing degradable polycations are combined within a single bilayer, or, alternatively, contained within distinct bilayers, either with or without the presence of non-degradable polycations.

In some embodiments, the nucleic acid present in the bilayer encodes a polypeptide such as, for example, endostatin, angiostatin, an inhibitor of vasoactive endothelial growth factor (VEGF), an inhibitor of a signal protein in a signaling cascade of vascular endothelial growth factor, and inhibitor of basic fibroblast growth factor (bFGF), an inhibitor of a signal protein in a signaling cascade of bFGF, or combinations thereof.

A wide range of implantable devices are adaptable for use in the present invention including, but not limited to, a stent, a pacemaker, a defibrillator, an artificial joint, a prosthesis, a neurostimulator, a ventricular assist device, congestive heart failure device, an indwelling catheter, an insulin pump, an incontinence device, a cochlear device, or an embolic filter.

In a second aspect, the present invention encompasses a method of delivering a nucleic acid into a cell. Such a method includes steps of contacting a cell with a polyelectrolyte assembly that is fabricated by layer-by-layer deposition of nucleic acid and polycation such that the assembly includes a nucleic acid/polycation bilayer. The nucleic acid is locally-delivered into the cell by contact with the polyelectrolyte assembly.

Methods of localized delivery of nucleic acid according to the invention are carried out in the presence of cell culture medium or, alternatively and more preferably, in the context of a medical device implanted in a living tissue.

In certain embodiments, the polyelectrolyte assembly includes at least two nucleic acids that differ by nucleotide sequence. These respective nucleic acids reside in different bilayers and, in carrying out the method, are sequentially delivered into the cell.

In a third aspect, the invention is directed to a method of providing an implantable medical device capable of localized delivery of nucleic acid to a cell in contact with or located at an implantation site of the respective device. The method includes steps of layer-by-layer depositing nucleic acid and polycation on a surface of an implantable medical device to provide a polyelectrolyte assembly coating at least a portion of the implantable medical device. The polyelectrolyte assembly includes at least one nucleic acid/polycation bilayer.

The devices and methods of the present invention are advantageous in that they allow for the fabrication of an implantable medical device that is customized for the need of a subject. According to the present invention a device can be coated with a film comprising a nucleic acid sequence that locally transfects cells of a subject in situ providing for the production of therapeutic agents that facilitate a certain therapeutic activity including, for example, the acceptance of the device by the subject through the reduction of inflammation associated with implant placement.

Other objects, features and advantages of the present invention will become apparent after review of the specification, claims and drawings.

BRIEF DESCRIPTION OF THE DRAWINGS

FIG. 1A) Idealized scheme showing layer-by-layer fabrication of a multilayered film fabricated from alternating layers of degradable polymer 1 (dark shading) and a plasmid DNA encoding a fluorescent protein (pEGFP) (light shading). Incubation of this material under physiological conditions results in the gradual release of DNA.

DETAILED DESCRIPTION OF THE INVENTION

I. In General

Figure 1:
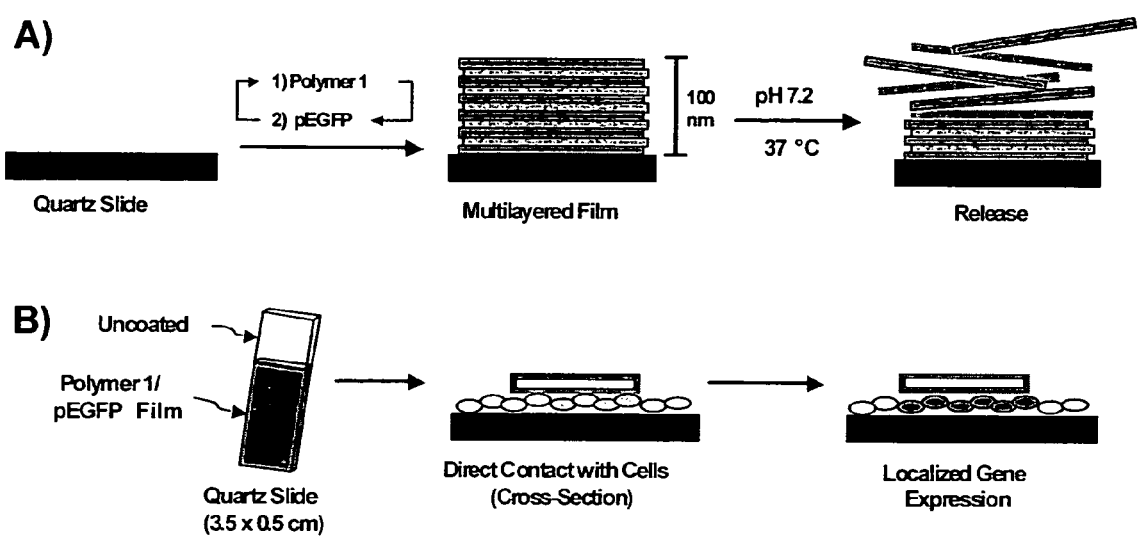
FIGS. 1A and B.
FIG. 1B) General scheme illustrating the direct and localized transfection of cells using a quartz slide coated with a polymer 1/DNA film. Coated quartz slides are placed manually on top of cells growing on the surface of a tissue culture dish.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

II. The Invention

The present invention is based on the inventors' discovery that particular polyelectrolyte assemblies fabricated by the sequential adsorption of nucleic acid and synthetic degradable cationic polymers can be used to directly and locally deliver functional nucleic acid from the surfaces of film-coated macroscopic objects. Importantly, these polyelectrolyte films introduce the requisite combination of different chemical functionalities needed to deliver nucleic acid into cells in a tissue culture environment and promote significant levels of surface-localized gene expression without the need for any exogenous transfection agents. These polyelectrolyte materials therefore present an advantageous structural framework for the local or non-invasive delivery of one or more nucleic acids from the surfaces of, for example, implantable materials and biomedical devices.

The layer-by-layer deposition of polyelectrolytes is a convenient and well-established method for the incorporation of natural and synthetic polyelectrolytes into thin nanostructured assemblies (C. S. Peyratout, L. Dahne, Tailor-made polyelectrolyte microcapsules: from multilayers to smart containers. *Angew Chem Int Ed Engl* 2004, 43, 3762-83). The technique takes advantage of electrostatic attractive forces between charged polymers and oppositely-charged surfaces, and film growth is typically achieved stepwise by the repetitive exposure of substrates to dilute polycation and polyanion solutions. Using this approach, it is possible to control film thickness on the nanometer scale simply by increasing the number of adsorbed polycation/polyanion layers, or to fabricate films possessing gradients of different polyelectrolyte components by manipulating the sequences in which multiple different polymer components are adsorbed. Multilayered films have been applied in numerous biological and therapeutic contexts (T. Groth, A. Lendlein, Layer-by-Layer Deposition of Polyelectrolytes—A Versatile Tool for the In Vivo Repair of Blood Vessels. *Angew Chem Int Ed Engl* 2004, 43, 926-928.), but the stability of these ionically crosslinked networks under physiological conditions has been an obstacle to the design of films that erode or disintegrate in a controlled manner in biological environments. Schüler et al., for example, demonstrated that herring sperm DNA could be released from polyelectrolyte assemblies fabricated from a low molecular weight polyamine upon changes in ionic strength (C. Schuler, F. Caruso, Decomposable hollow biopolymer-based capsules. *Biomacromolecules* 2001, 2, 921-926.), however disruption was reported to require changes in ionic strength that were significantly outside the physiological range.

The inventors have presently demonstrated that polycation and DNA-containing composites can be used to localize the release of DNA to cells from the surfaces of film-coated objects directly and self-sufficiently (i.e., without the aid of any additional transfection agents). These films are able to promote the localized transfection of cells in culture, and, while not adopting any one particular method of operation herein, these assemblies ultimately appear to present surface bound DNA in a nanoparticulate morphology that contributes to enhanced cell internalization. Thin films and conformal coatings that effectively combine the surface localization of DNA with polycationic transfection reagents are useful in various medical applications including, but not limited to, localized gene therapy and the growth or regeneration of complex tissues and ameliorating the pathophysiological effect of medical device implantation. As used herein, the terms "transformation" and "transfection" are intended to refer to techniques for introducing foreign nucleic acid (e.g., DNA) into a target or host cell.

Accordingly, the present invention provides a method of promoting delivery of a nucleic acid to a cell. Such method includes the step of contacting a cell with a polyelectrolyte assembly that is fabricated by layer-by-layer deposition of nucleic acid and polycation upon any suitable substrate, wherein the nucleic acid is directly and locally-delivered to the cell upon degradation or physical erosion of the polycation.

In general, polycations useful in the present invention are degradable or erodable polymers with cationic groups distributed along the polymer backbone. The cationic groups, which may include protonated amine, quaternary ammonium or phosphonium derived functions, may be disposed in side groups pendant from the backbone, may be attached to the backbone directly, or can be incorporated in the backbone itself.

Polycations suitable for use in the present invention include, but are not limited to, poly(beta-amino ester)s, polyethyleneimines or polyphosphoesters (Peterson, H. et al., (2002) Poly(ethyleneimine-co-L-lactamide-co-succinamide): A Biodegradable Polyethyleneimine Derivative with an Advantageous pH-Dependent Hydrolytic Degradation for Gene Delivery. Bioconjugate Chem., 13, 812-821; Wang, J., Mao, H., Leong, K. W. (2001) A Novel Biodegradable Gene Carrier Based on Polyphosphoester. J. Am. Chem. Soc., 123, 9480-9481; Lim, Y.; et al., (2000) Development of a Safe Gene Delivery System Using Biodegradable Polymer, Poly [alpha-(4-aminobutyl)-L-glycolic acid]. J. Am. Chem. Soc., 122, 6524-6525; Lynn, D. M., Langer, R. (2000) Degradable Poly(.beta.-Amino Esters): Synthesis, Characterization, and Self-Assembly with Plasmid DNA J. Am. Chem. Soc., 122, 10761-10768; Putnam, D., Langer, R. (1999) Poly(4-hydroxy-1-proline ester): Low-Temperature Polycondensation and Plasmid DNA Complexation. Macromolecules, 32, 3658-3662.

Polycations belonging to the family of poly(beta-amino esters), of which, literally, thousands have been synthesized, are particularly useful in the present invention. The general structure and illustrative species of poly(beta-amino ester)s are described in U.S. Ser. No. 09/969,431, filed Oct. 2, 2001, entitled "Biodegradable poly(beta-amino esters) and uses thereof" and Lynn et al., J. Am. Chem. Soc. 122:10761-10768, 2000, the entire contents of both of which are incorporated herein by reference. Yet additional degradable polycations useful in the invention include, but are not limited to, the polycations disclosed in U.S. patent application Ser. No. 10/280,268, filed Oct. 24, 2002, entitled "Methods of making decomposable thin films of polyelectrolytes and uses thereof," which is incorporated herein by reference.

Figure 3:
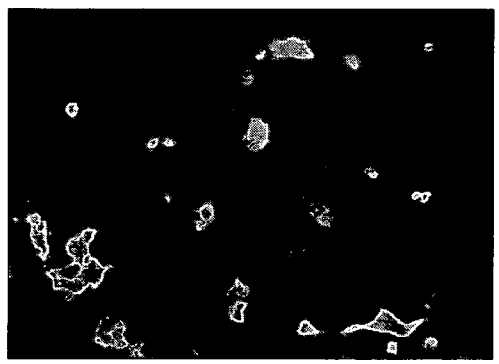
FIGS. 3 A and B: Fluorescence microscopy images showing the expression of EGFP and the localization of transfection in COS-7 cells. Direct transfection was mediated using a quartz substrate functionalized on a single side with a thin multilayered film composed of eight layers of polymer 1 and pEGFP plasmid. These images were recorded after 48 hours of contact with the film-coated substrate. A) An image recorded through a 10× objective showing transfected cells. B) An image recorded through a 4× objective showing the extent to which transfection was localized to cells growing under the film-coated substrate. The dotted line in this image indicates the edge of the film-coated substrate.
Figure 3:
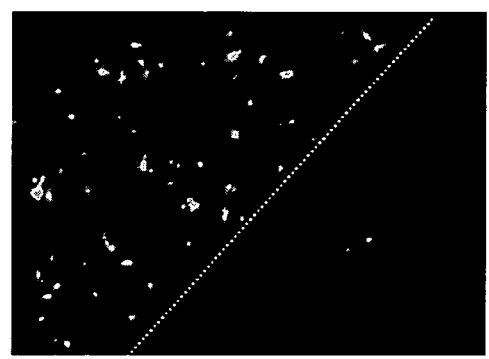

Illustrative poly(beta-amino ester)s are shown in FIG. 3. of U.S. patent application Ser. No. 10/280,268. Exemplary constituent groups present in the poly(beta-amino ester)s include hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups. As described in the references cited above, poly(beta-amino ester)s are commonly prepared from the conjugate addition of primary or secondary amines to diacrylates. Typically, poly(beta-amino ester)s have one or more tertiary amines in the backbone of the polymer, generally one or two per repeating backbone unit. The polymer may have between 5 and 10,000 repeat units.

In addition, a range of hydrolytically degradable amine containing polyesters bearing cationic side chains have recently been developed (Putnam et al. Macromolecules 32:3658-3662, 1999; Barrera et al. J. Am. Chem. Soc. 115:11010-11011, 1993; Kwon et al. Macromolecules 22:3250-3255, 1989; Lim et al. J. Am. Chem. Soc. 121:5633-5639, 1999; Zhou et al. Macromolecules 23:3399-3406, 1990; each of which is incorporated herein by reference). Examples of these polyesters include poly(L-lactide-co-L-lysine) (Barrera et al. J. Am. Chem. Soc. 115:11010-11011, 1993; incorporated herein by reference), poly(serine ester) (Zhou et al. Macromolecules 23:3399-3406, 1990; which is incorporated herein by reference), poly(4-hydroxy-L-proline ester) (Putnam et al. Macromolecules 32:3658-3662, 1999.; Lim et al. J. Am. Chem. Soc. 121:5633-5639, 1999; each of which is incorporated herein by reference), and more recently, poly[alpha-(4-aminobutyl)-L-glycolic acid].

Zwitterionic polyelectrolytes may also be incorporated into polyelectrolyte assemblies useful in the present invention. Such polyelectrolytes may have both anionic and cationic groups incorporated into the backbone or covalently attached to the backbone as part of a pendant group. Such polymers may be neutrally charged at one pH, positively charged at another pH, and negatively charged at a third pH. For example, a film may be deposited by layer-by-layer deposition using dip coating in solutions of a first pH at which one layer is anionic and a second layer is cationic. If the film is put into a solution having a second different pH, then the first layer may be rendered cationic while the second layer is rendered anionic, thereby changing the charges on those layers.

Certain methods according to the present invention utilize polyelectrolyte assemblies including dynamic charge state cationic polymers. Dynamic charge state cationic polymers are useful for delivery of anionic molecules and exemplary polymers and methods are disclosed in U.S. patent application Ser. No. 10/886,161, filed Jul. 7, 2004, entitled "Charge dynamic polymers and delivery of anionic compounds," which is incorporated by reference herein in its entirety. Dynamic charge state cationic polymers are designed to have cationic charge densities that decrease by removal of removable functional groups from the polymers.

Assemblies useful in the present invention are constructed on the surface of a substrate. A variety of materials can be used as substrates such as, but not limited to, metals, e.g., gold, silver, platinum, and aluminum; metal-coated materials; metal oxides; plastics; ceramics; silicon; glasses; mica; graphite; hydrogels; polymers and combinations thereof. A substrate of one material may be coated with a second material, or two materials may be combined to form a composite. Particularly useful substrates include, but are not limited to degradable or non-degradable biocompatible polymers and biocompatible metal alloys commonly used to manufacture or fabricate implantable medical devices and drug delivery implements. The size of the substrate is not limited and can be macroscopic or can have physical dimensions on the order of micrometers or nanometers. As would be apparent to one of ordinary skill in the art, the substrate surface can be pretreated or modified in any number of suitable and desirable ways prior to the deposition of the polyelectrolyte assembly.

The preferred manufacturing method for the polyelectrolyte assemblies is set forth in the examples section below. In general, films may be fabricated from polycation and nucleic acid using any of the generally accepted methods known to those of skill in the art including, but not limited to, dip coating, spray coating, brush coating, roll coating, spin casting, or combinations thereof. In one particularly useful method, substrates or solid objects may be coated using a manual or automated dipping protocol similar to those reported previously for polycation/DNA systems (J. Zhang, L. S. Chua, D. M. Lynn, Multilayered Thin Films that Sustain the Release of Functional DNA Under Physiological Conditions. *Langmuir* 2004, 20, 8015-8021). Briefly: 1) A substrate is submerged in a solution of polycation for a length of time suitable to allow sufficient adsorption of polycation to the substrate, 2) the substrates is removed and immersed in one or several wash baths, the substrate is submerged in a solution of nucleic acid for a length of time suitable for the adsorption of nucleic acid, and 4) the substrate is again washed or rinsed in the manner described above for step 2. This cycle is generally repeated until the desired number of polymer and DNA layers have been deposited or the desired thickness of the deposited assembly has been reached.

The term "multilayered films", as used herein, shall refer to films having at least one "bilayer" of deposited material. The term "bilayer", as used herein, shall refer to the accumulated layers of material deposited on a surface as a result of having passed through at least one complete cycle of the general steps 1-4 identified above. Preferred embodiments utilize films having at least two bilayers of nucleic acid and polycation. More preferred embodiments utilize films having at least four bilayers of nucleic acid and polycation. In certain embodiments, at least two of the nucleic acid layers include nucleic acids characterized by differing nucleotide sequences. The sequential delivery of differing nucleic acids to a cell is therefore contemplated by the present invention. Layer-by-layer fabrication, also termed LBL fabrication, offers an opportunity to design films containing spatially segregated regions of polyelectrolyte confined to different regions of a film (i.e., in either the top or the bottom). It is therefore possible to use the layered nature of these materials to fabricate assemblies that release different concentrations of multiple plasmids or to control the kinetics with which two differing nucleic acids are released by incorporating intermediate polyelectrolyte layers that erode more slowly.

In certain embodiments, the composition of the nucleic acid and polycationic layers can be fine-tuned to adjust the degradation rate of each layer within the film. For example, the degradation rate of hydrolytically degradable polyelectrolyte layers can be decreased by associating hydrophobic polymers such as hydrocarbons and lipids with one or more of the layers. Alternatively, the polyelectrolyte layers may be rendered more hydrophilic to increase their hydrolytic degradation rate. In certain embodiments, the degradation rate of a given layer can be adjusted by including a mixture of polyelectrolytes that degrade at different rates or under different conditions. In other embodiments, the nucleic acid and/or polycationic layers may include a mixture of degradable and non-degradable polyelectrolytes. Any non-degradable polyelectrolyte can be used with the present invention. Exemplary non-degradable polyelectrolytes that could be used in thin films of the present invention include poly(styrene sulfonate) (SPS), poly(acrylic acid) (PAA), linear poly(ethylene imine) (LPEI), poly(diallyldimethyl ammonium chloride) (PDAC), and poly(allylamine hydrochloride) (PAH).

Alternatively or additionally, the degradation rate may be fine-tuned by associating or mixing non-biodegradable, yet biocompatible polymers (polyionic or non-polyionic) with one or more of the nucleic acid and/or polycationic layers. Suitable non-biodegradable, yet biocompatible polymers are well known in the art and include polystyrenes, certain polyesters, non-biodegradable polyurethanes, polyureas, poly (ethylene vinyl acetate), polypropylene, polymethacrylate, polyethylene, polycarbonates, and poly(ethylene oxide)s.

Furthermore, because the thin film is produced in a layer-by-layer fashion, the composition of individual layers may be varied to tailor the degradation rate of various portions of the film. For example, the upper layers of the film, closer to the surface, may be adjusted to degrade faster than the layers of the film closer to the substrate, or vice versa. Depending on the thickness of the film, the degradation rate within the film may be varied cyclically (e.g., for periodic release). Additionally or alternatively, the upper layers of the film, closer to the surface, may be adjusted to degrade under a first set of conditions (e.g., endosomal conditions) while the layers of the film that are closer to the substrate are adjusted to degrade under a second set of conditions (e.g., physiological conditions).

As noted above, polyelectrolytes may be associated or mixed with polymeric or non-polymeric moieties to regulate the degradation rate. In addition, neutral, zwitterionic, or charged biomolecules, small molecules, or bioactive agents may be associated or mixed with a polycation or nucleic acid and incorporated into a layer. For example, the charged atoms on a zwitterionic molecule may facilitate electrostatic interactions with both the nucleic acid and polycationic layers. A zwitterionic biomolecule, small molecule, or bioactive agent may be combined in solution with the polyelectrolytes for one of the layers or placed in a separate solution to form a "sandwich" between two layers. When the thin film degrades, the biomolecule, small molecule, or bioactive agent will be released. Alternatively, a biomolecule, small molecule, or bioactive agent may be associated with a polyelectrolyte under conditions which facilitate a strong interaction between the molecule and the polyelectrolyte, while the medium in which the biomolecule, small molecule, or bioactive agent is released is one which competes with the polyelectrolyte for the biomolecule, small molecule, or bioactive agent, thereby decreasing the strength of the interaction with the polyelectrolyte.

The composition of the various layers may be adjusted to release different entities in addition to the nucleic acid as the thin film degrades. For example, a thin film may be designed to release therapeutic agents such as chemotactic factors tailored to attract or inhibit the growth of cells at an implant site, followed by a nucleic acid to transfect and affect/alter gene expression related to a desired metabolic or proliferative activity in cells now at the implant site. For example, such therapeutic agents may include growth factors such as EGF, bFGF, their inhibitors, receptor agonists or receptor antagonists, neuropeptides and their agonists or antagonists and nucleic acids coding for such therapeutic agents.

It will be appreciated that in preparing a thin film that degrades with a desired rate and profile one may need to test various thin film compositions experimentally. The degradation rates and profiles of inventive thin films can, for example, be investigated using a variety of known techniques, including ellipsometry, dynamic light scattering (DLS), zeta-potential analysis, quartz crystal microbalance (QCM), and atomic force microscopy (AFM). The QCM method is particularly attractive since it can be used with rough films and allows continuous monitoring without removal of the thin films from the degradation milieu. AFM can be also used to monitor changes in the multi-layer surface morphology as a function of degradation.

Additionally or alternatively, one may choose to monitor the rate at which a non-degradable structural polymer, biomolecule, small molecule, nucleic acid or bioactive agent is released from the thin film. If the released entity absorbs or emits light in an un-crowded region of the ultraviolet or visible electromagnetic spectrum, one could measure the rate of release by UV-visible spectroscopy. It will be appreciated that a variety of synthetic and recombinant techniques exist that allow one to attach a light absorbing or emitting group, e.g., a fluorescent group or a dye to a polymer or small molecule that lacks such functionality. Alternatively, one could incorporate a model chromic compound, e.g., the commercially available photochromic polyanion PAZO, into a range of thin films for this purpose.

Nucleic acid delivered by a method according to the invention is preferably in the form of deoxyribonucleic acid (DNA), more preferably in the form of a DNA vector, most preferably an expression vector. Alternatively, the inventive method may convey ribonucleic acid or, in yet other alternative embodiments, a protein/nucleic acid (PNA) molecule or other mimetic understood by one of skill to be a nucleic acid equivalent. As used herein, the term "nucleic acid" generally refers to any polyribonucleotide or polydeoxribonucleotide, which may be unmodified RNA or DNA or modified RNA or DNA. "Nucleic acids" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions.

In addition, "nucleic acid" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "nucleic acid" also includes DNAs or RNAs as described above that contain one or more modified bases. Thus, DNAs or RNAs with backbones modified for stability or for other reasons are "nucleic acids" as that term is intended herein. Moreover, DNAs or RNAs comprising unusual bases, such as inosine, or modified bases, such as tritylated bases, to name just two examples, are nucleic acids as the term is used herein. It will be appreciated that a variety of modifications have been made to DNA and RNA that serve many useful purposes known to those of skill in the art. The term "nucleic acid" as it is employed herein embraces such chemically, enzymatically or metabolically modified forms of nucleic acids, as well as the chemical forms of DNA and RNA characteristic of viruses and cells, including prokaryotic and eukaryotic cells. "Nucleic acid" also embraces short polynucleotides often referred to as oligonucleotide(s).

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors, referred to above, are termed "expression vectors". In general, expression vectors of utility in the present methods are in the form of plasmids. In the present specification, "plasmid" and "vector" can be used interchangeably as the plasmid is the most commonly used form of vector. However, the invention is intended to encompass the use of other forms of expression vectors, such as viral vectors (e.g., replication defective retroviruses, adenoviruses and adeno-associated viruses), which serve equivalent functions.

Expression vectors useful in the present invention include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence in the host cell. The term "regulatory sequence" is intended to include promoters, enhancers, and other expression control elements (e.g., polyadenylation signals). Such regulatory sequences are known in the art and described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the cell to be transfected, the level of expression of protein desired, and the like.

As well, the present invention encompasses the delivery of nucleic acids that provide the polynucleotide as an antisense agent or RNA interference (RNAi) agent (Fire et al. Nature 391:806-811, 1998; incorporated herein by reference in its entirety and for all purposes as if fully set forth herein). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular Mechanisms of Action of Antisense Drugs" Biochim. Biophys. Acta 1489(1):31-44, 1999; Crooke "Evaluating the Mechanism of Action of Antiproliferative Antisense Drugs" Antisense Nucleic Acid Drug Dev. 10(2):123-126, discussion 127, 2000; Methods in Enzymology volumes 313-314, 1999; each of which is incorporated herein by reference in its entirety and for all purposes as if fully set forth herein). The binding may be by conventional base pair complementarity, or, for example, in the case of binding to DNA duplexes, through specific interactions in the major groove of the double helix (i.e., triple helix formation) (Chan et al. J. Mol. Med. 75(4):267-282, 1997; incorporated herein by reference).

Methods according to the present invention are particularly suited to deliver nucleic acid to cells in the presence of cell culture medium, as demonstrated in the following examples section. However, it is further envisioned that the present invention is applicable to the delivery of nucleic acids to cells contained within living tissues, particularly to tissues present within a living "subject" or patient, preferably a human. As used herein the terms "subject" and "patient" mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The terms "subject" and "patient" do not denote a particular age or sex.

In certain embodiments, particularly for delivery of nucleic acids in a living entity, it may be desirable to target a nucleic acid to a particular cell or tissue. A variety of agents that can direct a substrate to particular cells are known in the art (see, for example, Cotten et al., *Methods Enzym.* 217:618, 1993). Examples of useful targeting agents include, but are in no way limited to, low-density lipoproteins (LDLs), transferrin, asiaglycoproteins, gp120 envelope protein of the human immunodeficiency virus (HIV), toxins, antibodies, and carbohydrates. Certain methods according to the present invention call for one or more targeting agents to be associated with polyelectrolyte components of the film and/or with the nucleic acid entity to be released.

For example, in one exemplary embodiment or strategy of the invention, plasmid DNA or viral vector is incorporated into a stent coating, or other the coating of another implantable device which comprises a polycationic bilayer, such as polymer 1, that adheres to the stent and incorporates the DNA or viral vector, or transformed cells, without damaging them. Thereby the coating facilitates DNA delivery to, and transfection of, cells within the local area of the stent such as, for example, an injured vessel wall. The nucleic acid within the stent coating may encode gene products with a variety of therapeutic activities including, but not limited to, anti-restenosis activities. The coating can be formed using any polycationic polymer as discussed previously.

The layer-by-layer assembly approach used to manufacture useful films provides control over the location and distribution of nucleic acid in thin, nanostructured films that can be fabricated conformally onto a variety of complex macroscopic substrates. The substrate geometry may be manipulated to deposit films having a variety of shapes. For example, films may be deposited on particles, tubes, or spheres to facilitate a more uniform release distribution. Films may be deposited on strands such as sutures to release nucleic acids at a surgical site. Alternatively, these films may be deposited onto capillary networks or tissue engineering constructs. As previously-noted, a thin film deposited on a three-dimensional tissue engineering construct may be used to attract cells to a newly implanted construct and then to promote specific metabolic or proliferative activity. As such, the materials and approaches reported here could represent an attractive framework for the local or non-invasive delivery of nucleic acid from the surfaces of implantable materials or biomedical devices. The invention provided herein introduces new opportunities to design more advanced layered materials that enhance or influence further the mechanisms through which nucleic acid and other biological materials are internalized. As can be appreciated, the methods described herein encompass the manufacture of multi-layer film-coated implantable materials or biomedical devices (e.g., film-coated stent, pacemaker, prosthesis, catheters etc.). In view of the above discussion it will be understood that the invention involves certain devices and methods useful to deliver gene products to cells at implantation sites. In particular, the terms "local" and "localized," when referring herein to nucleic acid delivery in the context of living cells or tissues, shall mean delivery of nucleic acid to cells in direct contact with, or in the near vicinity of, a portion of a device coated with polyelectrolyte assembly.

The therapeutic agents used in this invention can be any gene encoding a protein that has been demonstrated to have, or is suspected of having, beneficial effects. Examples include, but are not limited to, endostatin and angiostatin. Other examples include, but are not limited to, genes that encode a product that inhibits the effects of known or as yet unknown agents that facilitate restenosis, by either binding to the agent and preventing its activity, by binding to its receptor, or by inhibiting any aspect of the signaling cascade initiated by the binding of the agent to its receptor. Examples of targets for anti-restenosis strategies would include, but not be limited to VEGF, its receptors, and its signaling cascade; and bFGF, its receptors, and its signaling cascade The examples disclosed herein show that multilayered polyelectrolyte films fabricated from plasmid DNA and hydrolytically degradable polyamines permit spatial and temporal control over the release of DNA from surfaces (C. M. Jewell, et al., Multilayered Polyelectrolyte Films Promote the Direct and Localized Delivery of DNA to Cells. *J. Control. Release* 2005, 106, 214-223). For example, multilayered films 100 nm thick fabricated from degradable poly(β-amino ester) 1 and plasmid DNA encoding green fluorescent protein erode gradually and release DNA over a period of one to two days when incubated in PBS buffer. Significantly, the DNA released from these films remains transcriptionally active, and the inventors have demonstrated that planar objects (e.g., glass slides) coated with these ultrathin films can be used to mediate the localized and contact-mediated transfection of cells in serum-containing cell culture media. These results suggest the basis of an approach that could be used to localize the delivery of plasmid DNA from the surfaces of topologically complex implantable materials and devices.

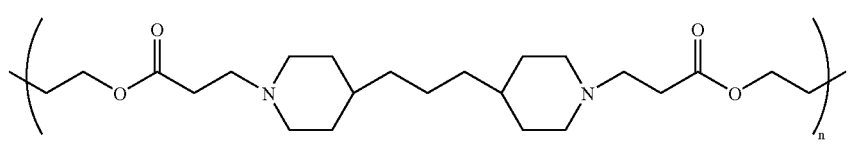

Polymer 1

In the context of controlled release, the layer-by-layer approach described above offers several potential advantages relative to conventional methods for the bulk encapsulation of DNA or other methods recently reported for the immobilization and release of DNA from surfaces (B. D. Klugherz, et al., Gene delivery from a DNA controlled-release stent in porcine coronary arteries. *Nat Biotechnol* 2000, 18, 1181-4; Y. Nakayama, et al., Development of high-performance stent: gelatinous photogel-coated stent that permits drug delivery and gene transfer. *J Biomed Mater Res* 2001, 57, 559-66; T. Segura, L. D. Shea, Surface-tethered DNA complexes for enhanced gene delivery. *Bioconjugate Chemistry* 2002, 13, 621-629). First, layer-by-layer fabrication offers a straight-forward mechanism for control over the amount of DNA incorporated into a film by control over the numbers of layers of polymer and DNA deposited. Second, the process used to fabricate these films is entirely aqueous and does not involve the exposure of the DNA or the film itself to organic solvents that could remain in these materials after fabrication. Third, because the DNA in these multilayered assemblies is packaged between alternating layers of cationic polymer (a class of materials that is used broadly to transfect cells), these thin films could potentially be designed to participate actively in the packaging, presentation, and internalization of DNA by cells. Finally, the scope of objects that can be coated with multilayered films is broad, and includes materials such as stainless steel and other materials known to the artisan for construction of implantable devices ranging from vascular stents and prosthesis, such as artificial joints (e.g., hips) to other implantable therapeutics such as sutures, catheters and the like. Of particular relevance to the work reported here, Thierry et al. recently described the fabrication of multilayered films on the surfaces of nickel-titanium alloy wires and disks and the use of these films for the release of sodium nitroprusside, a nitric oxide donor used clinically to prevent restenosis, to vascular tissue (Thierry et al., Radionuclides-hyaluronan-conjugate thromboresistant coatings to prevent in-stent restenosis, Biomaterials. 2004 August; 25(17):3895-905).

The following examples illustrate that multilayered films ca. 100 nm thick fabricated from polyamine 1 and plasmid DNA encoding green fluorescent protein can be deposited homogeneously and conformally onto the surfaces of stainless steel stents using an entirely aqueous layer-by-layer fabrication procedure. Further, the examples show that these ultrathin coatings remain intact and substantially defect free after stent expansion and exposure to other physical challenges associated with stent deployment. In addition, the examples demonstrate that the DNA released from stents coated with these materials is able to mediate the transfection of mammalian cells in vitro. The results reported here support the utility of the present invention and, in particular, device-mediated approaches to the localized delivery of DNA to tissues.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

Multilayered Films Promote the Direct and Localized Delivery of Nucleic Acid to Cells A. Materials.

Linear poly(ethylene imine) (LPEI, MW=25,000) was obtained from Polysciences, Inc. (Warrington, Pa.). Poly(sodium 4-styrenesulfonate) (SPS, MW=70,000) and sodium acetate buffer were purchased from Aldrich Chemical Company (Milwaukee, Wis.). All commercial polyelectrolytes were used as received without further purification. Plasmid DNA [pEGFP-N1 or pDsRed2 (4.7 kb), >95% supercoiled] was obtained from a commercial supplier (Elim Biopharmaceuticals, Inc., San Francisco, Calif.). Polymer 1 (Mn=10,000), shown below, was synthesized as previously described by the inventors (D. M. Lynn, R. Langer, Degradable poly (beta-amino esters): Synthesis, characterization, and self-assembly with plasmid DNA. *J Am Chem Soc* 2000, 122, 10761-10768).

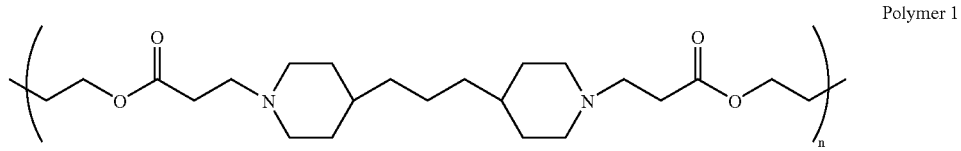

Polymer 1

For experiments requiring fluorescently labeled plasmid, Cy3 Label-IT nucleic acid labeling kits were purchased from Mirus Bio Corporation (Madison, Wis.) and used according to the manufacturer's instructions (labeling density=1 label: 320 base pairs). Deionized water (18 MΩ) was used for washing steps and to prepare all polymer solutions. PBS buffer was prepared by diluting commercially available concentrate (EM Science).

All buffers and polymer solutions were filtered through a 0.2 μm membrane syringe filter prior to use. Quartz substrates (3.5×0.5 cm) were cleaned with acetone, ethanol, methanol, and deionized water, dried under a stream of filtered air, and cleaned further by etching in an oxygen plasma etcher for 5 minutes (Plasma Etch, Carson City, Nev.) prior to film deposition. UV/vis absorbance values used to quantify film deposition were recorded on an Ultraspec 2100 Pro Spectrophotometer (Amersham Biosciences, Piscataway, N.J.) at a wavelength of 260 nm in at least three different locations on each sample. Atomic force microscopy images were obtained in tapping mode using a Nanoscope Multimode atomic force microscope (Digital Instruments, Santa Barbara, Calif.), using scan rates of 10-20 μm/s to obtain 256×256 pixel images. Silicon cantilevers with a spring constant of 40 N/m were used (model NSC15/NoAl, MikroMasch USA, Inc., Portland, Oreg.) and images were processed using the Nanoscope® IIIa software package (Digital Instruments, Santa Barbara, Calif.). Films fabricated from fluorescently labeled plasmid DNA were imaged using a Bio-Rad MRC-1024 Laser Scanning Confocal Microscope equipped with three excitation lines. Images were collected while exciting the films with the 568 nm laser and monitoring emission through a 585 nm long pass filter. Image processing was performed using Bio-Rad Laser Sharp Processing Kit and Adobe Photoshop 7.0. Ellipsometric thicknesses for films deposited on silicon substrates (used to estimate the thicknesses of films on quartz substrates) were determined using a Gaertner LSE Stokes Ellipsometer (632.8 nm, incident angle=70°). Data were processed using the Gaertner Ellipsometer Measurement Program software package. Relative thicknesses were calculated assuming an average refractive index of 1.55 for the multilayer films.

B. Preparation of Polyelectrolyte Solutions

Solutions of polymer 1 used for dipping (5 mM with respect to the molecular weight of the polymer repeat unit) were prepared in sodium acetate buffer (100 mM, pH=5.0) and filtered through a 0.2 μm membrane syringe filter prior to use. Solutions of LPEI and SPS used for the fabrication of LPEI/SPS precursor layers (20 mM with respect to the molecular weight of the polymer repeat unit) were prepared using 18MΩ water and adjusted to pH 5.0 using HCl. Solutions of plasmid DNA were prepared at a concentration of 1 mg/mL in acetate buffer (100 mM, pH=5.1) and were not filtered prior to use.

C. Fabrication of Multilayered Films

Films fabricated from polymer 1 and plasmid DNA encoding either enhanced green fluorescent protein (EGFP) or red fluorescent protein (RFP) were fabricated using an optimized dipping protocol similar to that reported previously for these polymer/DNA system. All polymer/DNA films were deposited on quartz slides precoated with 10 bilayers of linear poly(ethylene imine) and poly(styrene sulfonate) to ensure a suitably charged surface for the adsorption of polymer 1. Polymer 1/DNA layers were deposited on these foundation layers using a manual dipping process. Briefly: 1) Substrates were submerged in a solution of polymer 1 for 5 minutes, 2) substrates were removed and immersed in a wash bath for 1 minute followed by a second wash bath for 1 minute (wash baths were either deionized water or 100 mM sodium acetate buffer, pH=5.0), 3) substrates were submerged in a solution of plasmid DNA for 5 minutes, and 4) substrates were rinsed in the manner described above. This cycle was repeated until the desired number of polymer and DNA layers (typically eight each) had been deposited. For slides coated on only one side (see text), commercially available rubber cement was painted on one face of the slide and allowed to dry prior to dipping. Removal of the rubber cement by peeling after fabrication gave slides coated on one side and containing approximately 50% of the total DNA incorporated on two-sided slides, as determined by UV/vis spectrophotometry. The total amount of DNA incorporated into a film (per unit area of substrate) was determined by measuring the absorbance (at 260 nm) of DNA solutions obtained after complete erosion of a film in buffer, using methods similar to those described previously.

D. Localized Cell Transfection Experiments

COS-7 cells were grown in 6-well plates at an initial seeding density of 450,000 cells/well in 3.0 mL of growth medium (90% Dulbecco's modified Eagle's medium, 10% fetal bovine serum, penicillin 100 units/mL, streptomycin 100 microgram/mL). Cells were allowed to grow overnight to approximately 80% confluence and quartz slides coated with multilayered polymer 1/DNA films were placed manually into the wells on top of the cells (see FIG. 1). Cells were incubated for an additional 48 hours and both fluorescence and phase contrast images were recorded directly (without removal of the quartz slide) using an Olympus IX70 fluorescence microscope. Percentages of cells expressing EGFP were determined using the Metavue version 4.6 software package (Universal Imaging Corporation) and the Adobe Photoshop software package (Adobe Systems, Incorporated). The number of EFGP positive cells was counted in at least 5 different locations within a region of the culture well located beneath a film-coated quartz slide. The percentage of cells transfected was reported as an average relative to all cells in the corresponding phase contrast images.

Polymer 1 is cationic by virtue of protonation, it degrades via ester hydrolysis under physiologically relevant conditions, and it has been demonstrated to be biocompatible in several different contexts (S. R. Little, et al., Poly-beta amino ester-containing microparticles enhance the activity of nonviral genetic vaccines. *Proc Natl Acad Sci USA* 2004, 101, 9534-9). The inventors recently demonstrated that multilayered polyelectrolyte assemblies 100 nm thick could be fabricated from alternating layers of polymer 1 and plasmid DNA. These assemblies erode over a period of 30 hours under physiologically relevant conditions (FIG. 1A), and therefore function as a thin film platform for the sustained release of transcriptionally active DNA from surfaces. In this previous study, the inventors used a commercially available lipid-based transfection agent to demonstrate that the DNA recovered in solution was transcriptionally active.

The inventors fabricated films composed of eight alternating layers of polymer 1 and a plasmid (pEGFP-N1) encoding enhanced green fluorescent protein (EGFP) on planar quartz slides using a previously established alternating dipping procedure. Although multilayered films can in principle be deposited conformally onto a wide range of different surfaces, the inventors selected quartz slides for this present study to make possible quantitative characterization of film growth by UV/vis spectrophotometry and facilitate subsequent gene expression analyses by fluorescence microscopy. Quartz slides cut to fit precisely into the wells of a standard 6-well polystyrene tissue culture plate were pre-coated with a multilayered film composed of 10 bilayers of linear poly (ethylene imine) and poly(styrene sulfonate) (ca. 20 nm thick, with a topmost layer of SPS) to ensure a suitably charged surface for the adsorption of polymer 1. The deposition of eight alternating layers of polymer 1 and pEGFP plasmid onto these pre-coated substrates resulted in a linear increase in the absorbance of the films, consistent with the stepwise nature of the layer-by-layer growth process. Films fabricated in an identical manner on similarly prepared reflective silicon substrates were found to be ca. 100 nm thick, as determined by ellipsometry. Polymer 1/DNA films eight bilayers thick contained approximately 2.7 (+/−0.8) μg of DNA per $cm^2$, as determined by UV/vis spectrophotometric analysis of completely eroded films.

Figure 2:
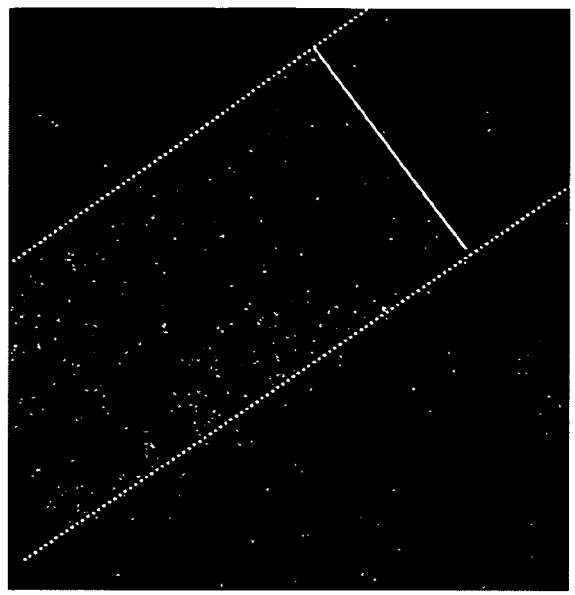
FIG. 2: A set of 35 adjacent low magnification (4×) fluorescence microscopy images showing localized transfection in a 1.5 cm² area of a confluent monolayer of COS-7 cells. Images were recorded 48 hours after exposure to a quartz substrate functionalized on both sides with erodible multilayered films fabricated from eight layers of polymer 1 and pEGFP. The solid white line (scale=0.5 cm) indicates the approximate location of the edge of the thin film on the quartz slide; portions of the quartz slide to the top and right of this line represent bare quartz used as a 'handle' during fabrication (see FIG. 1B). The dotted lines are placed at the edges of the quartz slide as a guide to the eye.

Film-coated slides were placed directly on top of COS-7 cells growing in 6-well culture plates in serum-containing culture medium (FIG. 1B). Cells were incubated for 48 hours in the presence of the coated slides and then analyzed by fluorescence microscopy. FIG. 2 presents a composite of adjacent low magnification (4×) images showing qualitatively the extent to which transfection was localized over a large 1.5 $cm^2$ portion of a culture well. These data demonstrate that films fabricated from polymer 1 are capable of delivering transcriptionally active DNA to cells in the presence of serum containing growth medium and in the absence of any additional transfection agents.

The majority of EGFP expression in these experiments was localized to cells growing underneath the film-coated portions of the slides. The inventors did not observe fluorescence in cells growing under bare, uncoated portions of the slides used as handles during the dipping-based fabrication procedure (FIG. 2, upper right; see also FIG. 1B). The inventors did, however, observe meaningful levels of non-localized expression in cells growing in adjacent areas of the culture well that were not in direct contact with or in the vicinity of the film-coated substrate. Because the dip-coating procedure the inventors used results in the conformal coating of all faces of a three-dimensional object (i.e., the front face, back face, and all sides of the quartz slide), the inventors considered the possibility that non-localized transfection could arise from the release of DNA or condensed polymer 1/DNA complexes from the top face of a slide, followed by diffusion and uptake by cells growing in adjacent regions of the culture well. To control for this possibility in subsequent experiments, the inventors fabricated slides coated on only one face by obscuring one side of the slide with a thin hydrophobic layer of rubber cement prior to film fabrication. Removal of the rubber cement after fabrication yielded slides coated with polymer 1/DNA on one side only. These slides contained 50% of the total amount of DNA incorporated on two-sided slides, as determined by UV/vis spectrophotometry.

When quartz slides coated on only one side were incubated face down on cells for 48 hours, EGFP expression was localized nearly exclusively to cells growing directly underneath the film-coated portion of the slide. FIGS. 3A and B presents two representative images showing cells expressing EGFP and the extent to which transfection was localized in these experiments. The average percentage of cells expressing EGFP relative to the total number of cells in a field of view ranged from 4.6% to 37.9%, with an average of 18.6%+/−8.2%, as determined by averaging counts of 35 fields of view taken from 7 individual experiments. The inventors previous solution-based release studies indicated that plasmid is completely released from 100 nm thick polymer 1/DNA films after about 30 hours upon incubation in phosphate buffered saline. Substrates removed from contact with cells after 24 hours and placed into contact with new unadulterated cultures did not result in the continued transfection of new cell populations, suggesting that film erosion may occur more rapidly in serum-containing cell culture medium.

E. Multilayer Film Erosion

Figure 4:
FIGS. 4A and B: Tapping mode atomic force microscopy image showing a 10 μm×10 μm area of an eight bilayer polymer 1/plasmid film fabricated on silicon using acetate buffer for washing steps and imaged A) before and B) one hour after incubation in PBS buffer (scale in z direction is 200 nm). C) Confocal scanning laser microscopy image of a film fabricated from five bilayers of polymer 1 and Cy3-labeled plasmid deposited on a glass microscope slide. The white scale bar represents 25 μm.
Figure 4:
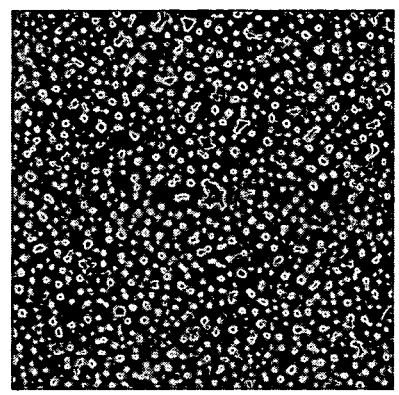
Figure 4:

To investigate further the mechanism of film erosion and the possible role of polymer 1 in the uptake and expression of plasmid by cells, the inventors used atomic force microscopy to analyze the surface morphologies of partially eroded polymer 1/DNA films. The inventors found that initially smooth polymer 1/DNA films (RMS roughness ca. 8-10 nm) undergo significant structural rearrangements upon incubation in phosphate buffered saline to present surface bound condensed plasmid DNA nanoparticles. FIGS. 4A and 4B show representative tapping mode AFM images of 10 µm×10 µm areas of an eight bilayer polymer 1/DNA film deposited on silicon FIG. 4A) before and FIG. 4B) one hour after incubation in PBS buffer. This image shows clearly the formation of round spherical structures on the surface with diameters ranging in size from 50 to 400 nm.

The inventors conducted an additional experiment using a film fabricated from polymer 1 and plasmid labeled with a Cy3 fluorescent dye to examine further the location of DNA in these films. FIG. 4c shows a confocal scanning laser microscopy image of a five-bilayer polymer 1/Cy3-pEGFP film deposited on a transparent microscope slide. This image shows clearly the presence of fluorescent punctate structures ranging in size from a few hundred nanometers to several microns in diameter. These data suggest that the DNA in these assemblies is condensed by polymer 1 upon incubation and presented at the surface of the film or substrate as particles that fall within the range of sizes required for efficient internalization by cells. The specific mechanisms through which cells interact with these materials and internalize incorporated DNA remains to be elucidated, and the inventors have found that fabrication conditions also influence significantly the surface morphologies of these materials. Without being held to any particular theory, the inventors hypothesize that polymer 1 may contribute to the condensation, internalization, and expression of plasmid in these surface-localized experiments. In any case, the juxtaposition of polycations with the DNA in these layered assemblies presents a clear set of design principles for the incorporation of other polycations (D. Luo, W. M. Saltzman, Synthetic DNA delivery systems. Nat Biotechnol 2000, 18, 33-37, hereby incorporated in its entirety) that could further influence cellular uptake and enhance DNA expression more effectively than polymer 1.

F. Multilayer Films Containing Alternating Layers of Differing Nucleic Acids.

The iterative nature of the layer-by-layer fabrication procedure used to fabricate the assemblies above also provides a convenient mechanism for the incorporation of more than one plasmid in a multilayered film. The inventors selected a second plasmid (pDsRed2-N1) encoding a red fluorescent protein (RFP) to fabricate films consisting of four bilayers of polymer 1/pEGFP (deposited first to form the bottom of the film) and four bilayers of polymer 1/pDsRed2 (deposited last to comprise the topmost portion of the film). The pDsRed2 plasmid is the same physical size (4 kb) as the pEGFP plasmid and these two plasmids exhibit identical deposition profiles, as determined using ellipsometry to analyze films fabricated on silicon substrates (data not shown). These (polymer 1/pEGFP)$_4$(polymer 1/pDsRed2)$_4$ films promoted the contact localized expression of both EFGP and RFP in cells. Significantly, both plasmids were expressed in cells simultaneously in these experiments. These results show that it is possible to layer multiple therapeutic agents in the bilayer and that various therapeutic agents can be delivered locally at the site of device implantation.

Example 2

Materials and Methods Related to the Coating of Implantable Devices with Multi-Layered Films A. Materials Poly(sodium 4-styrenesulfonate) (SPS, MW=70,000) and sodium acetate buffer were purchased from Aldrich Chemical Company (Milwaukee, Wis.). Linear poly(ethylene imine) (LPEI, MW=25,000) was obtained from Polysciences, Inc. (Warrington, Pa.). Polymer 1 was prepared as previously reported (See Example 1) and isolated by precipitation into hexane. Clinical grade plasmid DNA [pEGFP-N1 (4.7 kb), >95% supercoiled] was obtained from the Waisman Clinical BioManufacturing Facility at the University of Wisconsin—Madison. Test grade n-type silicon wafers were purchased from Si-Tech, Inc. (Topsfield, Mass.). 316L stainless steel coronary stents and deployment systems were obtained from Cordis (Miami, Fla.). Stents and catheter balloons were provided in sterile packages and had nominal diameters ranging from 2 mm to 5 mm and lengths ranging from 8 mm to 30 mm. Stent and balloon assemblies employed an over-the-wire type guidewire and expansion was performed using a standard inflation device and three-way valve with air or deionized water as the expansion fluid. Phosphate buffered saline was prepared by dilution of commercially available concentrate (EM science, Gibbstown, N.J.). Deionized water (18 MΩ) was used for washing steps and to prepare all buffer and polymer solutions. All buffers and polymer solutions were filtered through a 0.2 µm membrane syringe filter prior to use unless noted otherwise. Compressed air used to dry films and coated substrates was filtered through a 0.4 µm membrane syringe filter. All materials were used as received without further purification unless noted otherwise.

B. General Considerations

Silicon substrates (e.g., 0.5×3.0 cm) were cleaned with acetone, ethanol, methanol, and water and then dried under a stream of compressed air passed through a 0.2 µm filter. Surfaces were then activated by etching in an oxygen plasma for 5 minutes (Plasma Etch, Carson City, Nev.). Ellipsometric thicknesses of films deposited on silicon substrates were determined using a Gaertner LSE Stokes Ellipsometer (632.8 nm, incident angle=70°). Data were processed using the Gaertner Ellipsometer Measurement Program software package. Relative thicknesses were calculated assuming an average refractive index of 1.55 for the multilayer films. UV-visible absorbance values used to determine plasmid release kinetics were recorded on a Beckman Coulter DU520 UV/vis spectrophotometer (Fullerton, Calif.). Absorbance values were recorded at a wavelength of 260 nm in triplicate for all samples. For characterization of surface morphology by scanning electron microscopy (SEM), an accelerating voltage of 3 kV was used to obtain images on a LEO DSM 1530 scanning electron microscope. Samples were coated with a thin layer of gold using a sputterer (30 s at 45 mA, 50 mTorr) prior to imaging.

C. Preparation of Polyelectrolyte Solutions.

Solutions of polymer 1 used for dipping (5 mM with respect to the molecular weight of the polymer repeat unit) were prepared in sodium acetate buffer (100 mM, pH=5.0) and filtered through a 0.2 μm membrane syringe filter prior to use. Solutions of LPEI and SPS used for the fabrication of LPEI/SPS precursor layers (20 mM with respect to the molecular weight of the polymer repeat unit) were prepared using a 50 mM NaCl solution in 18 MΩ water. LPEI solutions contained 5 mM HCl to aid polymer solubility. Solutions of plasmid DNA were prepared at 1 mg/mL in sodium acetate buffer and were not filtered prior to use.

D. Fabrication of Multilayered Films.

Films fabricated from polymer 1 and plasmid DNA (pEGFP-N1) encoding enhanced green fluorescent protein were fabricated using a dipping protocol optimized for the deposition of this plasmid/polymer system on planar substrates. Polymer/DNA films were fabricated on either planar silicon substrates or stainless steel stents mounted and crimped on catheter balloon deployment systems. Prior to the fabrication of polymer/DNA films, substrates were precoated with 10 bilayers of a multilayered film composed of LPEI and SPS (ca. 20 nm thick, terminated with a topmost layer of SPS) to ensure a suitably charged surface for the adsorption of polymer 1, as previously described. Polymer 1/DNA layers were deposited on these foundation layers either manually or using an automated dipping robot (Model DR-3, Riegler & Kirstein GmbH, Berlin, Germany) using an alternating dipping procedure. Briefly: 1) Substrates were submerged in a solution of polymer 1 for 5 minutes, 2) substrates were removed and immersed in a wash bath of 100 mM sodium acetate buffer (pH=5.0) for 1 minute followed by a second wash bath for 1 minute, 3) substrates were submerged in a solution of plasmid DNA for 5 minutes, and 4) substrates were rinsed in the manner described above. This cycle was repeated until the desired number of polymer and DNA layers (typically eight) had been deposited. Stents coated using this procedure were either used immediately or dried under a stream of filtered compressed air and stored in a vacuum desiccator until use. All films were fabricated at ambient room temperature.

E. Mechanical Manipulation of Coated Stents

For experiments designed to evaluate the effects of stent expansion on film integrity and release profiles, balloon-mounted coated stents were attached to a syringe or standard inflation device and a pressure of 6-10 atm was applied by injecting air or deionized water into the balloon. The inflation pressure was maintained for 30 seconds, followed by aspiration of the fluid and removal of the stent from the balloon assembly. To characterize film integrity upon exposure to other mechanical forces typically encountered during stent deployment, coated stent/balloon assemblies were passed along a guide wire through the septum and shaft of an arterial inducer prior to expansion; the stent was subsequently expanded and removed from the catheter assembly as described above. Stents manipulated using these procedures were either used for analysis by SEM or used directly in subsequent erosion and release experiments.

F. Evaluation of Plasmid Release Kinetics

Experiments designed to investigate the erosion profiles of multilayered polymer 1/plasmid DNA stent coatings were performed in the following general manner: Film coated stents (either balloon-mounted or expanded, as described above) were placed in a plastic UV-transparent cuvette containing phosphate-buffered saline (PBS, pH 7.4, 137 mM NaCl) in an amount sufficient to cover the stent. The samples were incubated at 37° C. and removed at predetermined intervals to permit characterization of the incubation milieu by UV-visible spectrophotometry. After each measurement, stents were placed back into the cuvette, or, alternatively, into a new cuvette containing fresh PBS, and returned to the incubator.

G. Cell Transfection Assays

For experiments designed to evaluate the release profiles and integrity of released plasmid: COS-7 cells were grown in 96-well plates at an initial seeding density of 12,000 cells/well in 200 μL of growth medium (90% Dulbecco's modified Eagle's medium, 10% fetal calf serum, penicillin 100 units/mL, streptomycin 100 μg/mL). Cells were grown for 24 h, at which time a 50 μL mixture of Lipofectamine 2000 (Invitrogen, Carlsbad, Calif.) and plasmid solution was added directly to the cells according to the manufacturer's protocol. The lipid/plasmid transfection milieu was prepared by mixing 25 μL of the plasmid solution collected at each time point during release experiments (arbitrary concentrations but constant volumes) with 25 μL of diluted Lipofectamine 2000 reagent (24 μL stock diluted into 976 μL of serum-free culture medium). Fluorescence images were taken after 48 h using an Olympus IX70 microscope and analyzed using the Metavue version 4.6 software package (Universal Imaging Corporation). For experiments designed to evaluate the ability of coated stents to transfect cells in culture directly (i.e., in the absence of a secondary transfection agent): COS-7 cells were grown in 6-well plates at an initial seeding density of 150,000 cells/ml in 3.0 mL of growth medium (identical to the composition defined above). Cells were allowed to grow overnight to approximately 80% confluence and stents coated with multilayered polymer 1/DNA films were placed manually into the wells on top of and in direct contact with the cells. Cells were incubated for an additional 48 h and both fluorescence and phase contrast images were recorded directly using an Olympus IX70 fluorescence microscope.

Example 3

Fabrication of Erodible Films on the Surfaces of Intravascular Stents

One attribute of the layer-by-layer procedure used to fabricate multilayered polyelectrolyte films is that this procedure permits the fabrication of ultrathin films that conform to the surfaces of topologically complex objects. In principle, any solid surface that can be wetted by dilute, aqueous solutions of polyelectrolyte can be coated with a homogeneous and conformal multilayered film. The inventors fabricated multilayered films on the surfaces of surgical grade 316L stainless steel intravascular stents using polymer 1, a plasmid construct (pEGFP-N1) encoding EGFP, and an alternate dipping protocol optimized previously for the deposition of polymer 1/DNA films on planar silicon and quartz substrates as previously described in Example 1. In all cases, stents were precoated with a thin multilayered film (ca. 20 nm thick)

composed of sodium poly(styrene sulfonate) (SPS) and linear poly(ethylene imine) (LPEI) to provide a charged surface suitable for the adsorption of polymer 1. To investigate a range of different fabrication procedures, films were fabricated on 1) stents that were crimped and pre-mounted on balloon catheter assemblies (as received from the manufacturer) and 2) stents that were expanded and removed from the balloon assemblies prior to coating.

The inventors fabricated multilayered films composed of eight alternating layers of polymer 1 and pEGFP-N1 (referred to hereafter as eight 'bilayers') on the surfaces of stents having a variety of dimensions and strut geometries. The inventors showed, as described in Example 1, that the thicknesses of multilayered polymer 1/DNA films fabricated on silicon increase linearly with respect to the number of bilayers of material deposited, as determined by measuring periodic changes in optical thickness using ellipsometry. Ellipsometry is limited, however, by the general requirement that films be deposited on reflective, planar surfaces; this method cannot generally be used to characterize films on non-reflective substrates (e.g., unpolished stainless steel) or on topologically complex surfaces. To monitor the fabrication process and estimate the thicknesses of films deposited on stents, films were also fabricated on reflective silicon substrates precoated with a 20 nm thick film composed of 10 bilayers of SPS and LPEI, as described above. On the basis of this comparison, it is estimated the thicknesses of polymer 1/DNA films deposited onto stents are ca. 100 nm. These optical thickness values agree reasonably with values of film thickness estimated using scanning electron microscopy, as described below. Past studies suggest that polymer 1/DNA films eight bilayers thick contain DNA at a concentration of approximately 2.7 (+/− 0.8) $\mu g/cm^2$, as determined by UV absorbance.

Example 4

Physical Characterization of Coated Stents

Figure 5:
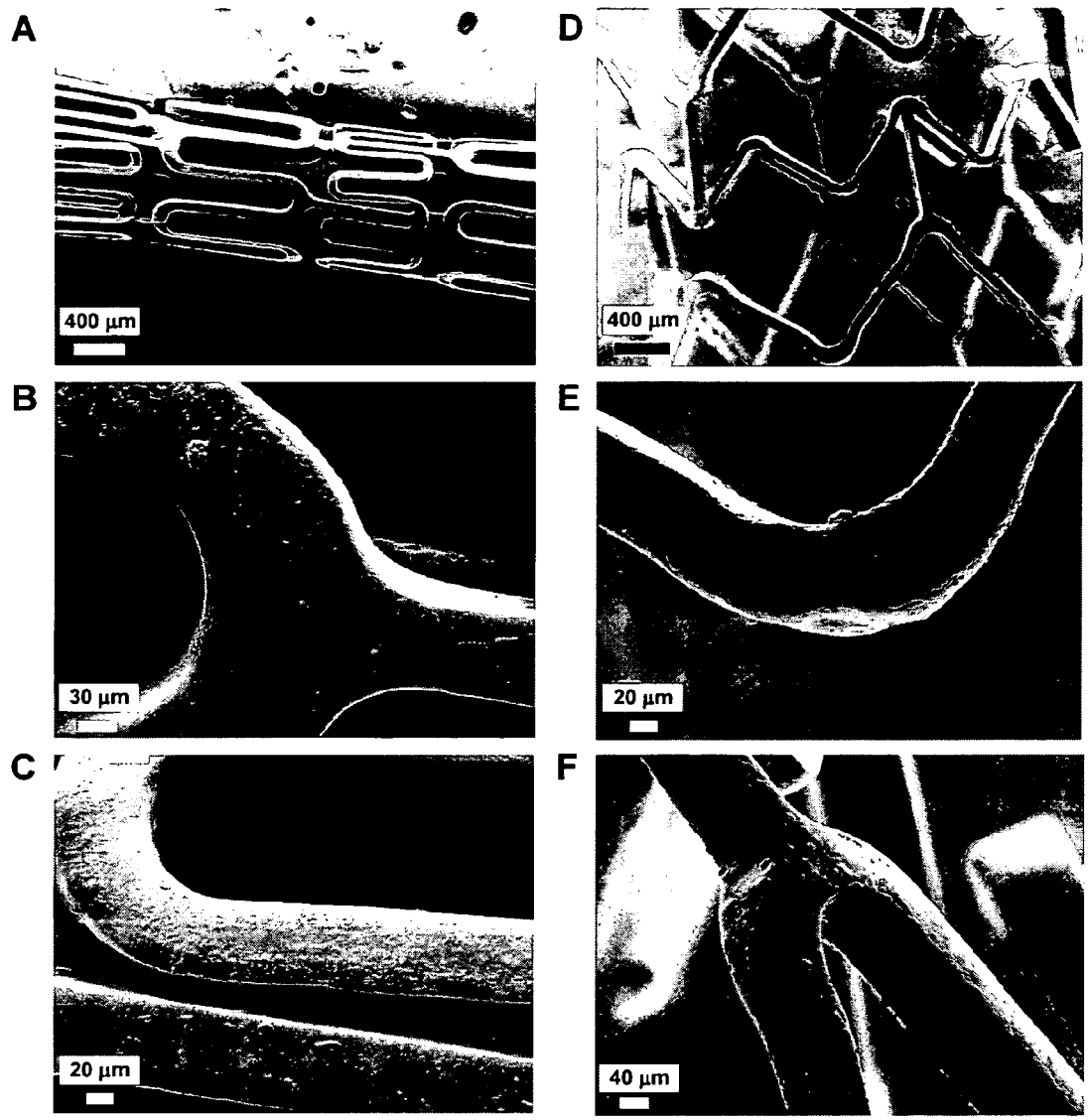
FIGS. 5 A-F are a scanning electron microscopy images of stainless steel intravascular stents coated with multilayed films fabricated from eight bilayers of polymer 1 and a plasmid DNA construct (pEGFP-N1) encoding enhanced green fluorescent protein. Stents were precoated with a thin multi-layered SPS/LPEI film (ca. 20 nm thick) prior to the deposition of the DNA-containing films. Images correspond to different magnifications and perspectives of a coated stent imaged as-coated on a balloon assembly (A-C) and after balloon expansion (D-F).

The inventors performed several experiments to characterize the surfaces of film-coated stents both immediately after fabrication and after exposure of the stents to mechanical forces associated with stent placement and deployment. FIGS. 5 A-C show representative scanning electron microscopy (SEM) images of a stent that was coated with an eight-bilayer film while crimped and mounted on a balloon assembly. These images demonstrate that the surface of the stent is coated uniformly with a thin film that conforms to the stent surface, the contours of the stent struts, and the balloon assembly. There was no observed presence of 'webs' of polymer or film stretched between stent struts or between stents and balloon assemblies, as has been reported previously for the encapsulation of DNA in thicker stent coatings fabricated using conventional materials and coating procedures. Further inspection of these images demonstrates that these ultrathin coatings are generally smooth and devoid of cracks or other significant defects over large areas of the stent surface.

Stent coatings are subject to a broad range of mechanical challenges during stent placement and deployment. For example, the coating on a stent must be able to pass unharmed through the septum and shaft of an arterial inducer, and the coating must also be compliant enough to withstand expansion of the stent without cracking, peeling, or delaminating from the stent surface. The inventors sought to determine whether the ultrathin polymer 1/DNA films fabricated above could withstand representative mechanical challenges associated with these procedures. FIGS. 5D-F show SEM images of a stent that was coated while mounted on a balloon assembly and then subsequently expanded prior to imaging. FIGS. 5E and 5F show higher magnification views of joints at the intersections of stent struts. These images demonstrate that the multilayered film did not crack, peel, or delaminate and that it remained conformal and adherent to the surface after the balloon expansion procedure.

Figure 6:
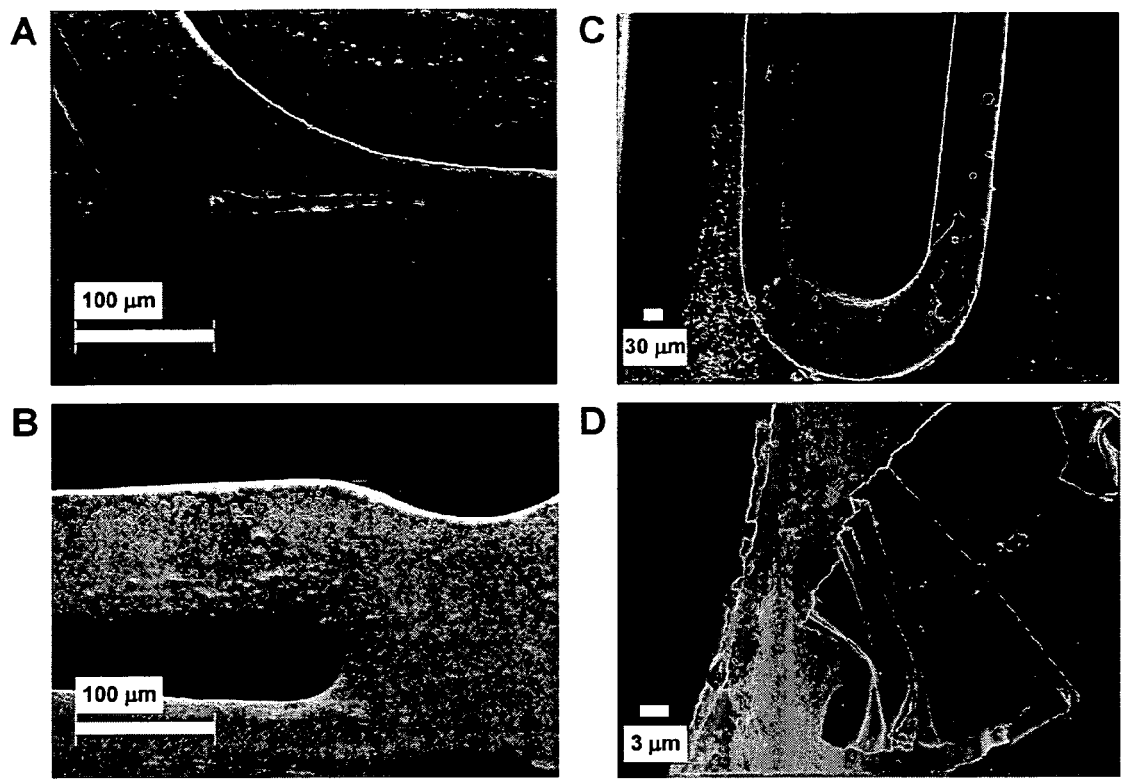
FIGS. 6 A-D Scanning electron microscopy images of intravascular stents coated with multilayered films fabricated from eight bilayers of polymer 1 and a plasmid DNA. Stents were coated while mounted on a balloon assembly and then passed through a silicone septum and arterial inducer prior to imaging.

FIGS. 6 A-D show representative images of a stent that was coated while mounted on a balloon assembly and then passed through the silicone septum and the shaft of an arterial inducer prior to imaging. These images demonstrate that the polymer 1/DNA films remain substantially intact and adherent to the stent surface after this procedure. In several cases, shallow scratches were observed in the film (FIG. 6A) and, in some cases, observed small micrometer-scale portions of the film that were peeled away from the stent surface (FIGS. 6C, 6D). However, the images in FIGS. 5 A-F and 6 A-D, when combined, demonstrate that ultrathin multilayered films fabricated from polymer 1 and plasmid DNA remain substantially intact after exposure to physical and mechanical challenges representative of those associated with stent deployment. Film defects such as the peeling observed in FIG. 6D provide an additional means with which to characterize the thicknesses of these ultrathin coatings. Such defects may be an artifact of mechanical handling of the stent during the implantation procedure. Physical film thicknesses of peeled or delaminated films were measured to be ca. 130 nm by computer image analysis of corresponding SEM images. These values are in reasonable agreement with the optical film thicknesses (ca. 100 nm) estimated by ellipsometry for films fabricated on silicon substrates (as described above).

Example 5

Characterization of Film Erosion and DNA Release Profiles

The layer-by-layer assembly of multilayered polyelectrolyte films is driven, in large measure, by multivalent interactions (e.g., electrostatic or hydrogen bonding interactions) that occur between oppositely charged polyelectrolytes. Owing to the strength of these multivalent interactions, many multilayered polyelectrolyte films are stable in physiological environments. The incorporation of hydrolytically degradable polyamines, such as polymer 1, into the structure of a multilayered film provides a mechanism with which to trigger or control film erosion in physiological media over periods of time ranging from two days to two weeks (J. Zhang, N. J. Fredin, D. M. Lynn, Erosion of Multilayered Films Fabricated from Degradable Polyamines: Characterization and Evidence in Support of a Mechanism that Involves Polymer Hydrolysis. *Journal of Polymer Science—Part A: Polymer Chemistry* 2006, 44, In Press). The inventors sought to characterize the physical erosion and DNA release profiles of polymer 1/DNA films coated onto the surfaces of stainless steel stents. In this context, it should be noted that several recent reports describe multilayered films fabricated from naturally occurring polyelectrolytes such as poly(amino acid)s, polysaccharides, or salmon sperm DNA that can be degraded in the presence of specific enzymes (K. F. Ren, J. Ji, J. C. Shen, Construction and enzymatic degradation of multilayered poly-L-lysine/DNA films. *Biomaterials* 2006, 27, 1152-1159), and that several other groups have reported multilayered films that erode or disintegrate in physiologically relevant environments (S. A. Sukhishvili, Responsive polymer films and capsules via layer-by-layer assembly. *Current Opinion in Colloid & Interface Science* 2005, 10, 37-44). In addition, the application of multilayered materials to the controlled release of small molecules and conventional drugs, which can be released by diffusion through multilayered films that need not physically degrade, is also an active and rapidly advancing area of research (M. C. Berg, et al., Controlled Drug Release from Porous Polyelectrolyte Multilayers. *Biomacromolecules* 2006, 7, 357-364).

Figure 7:
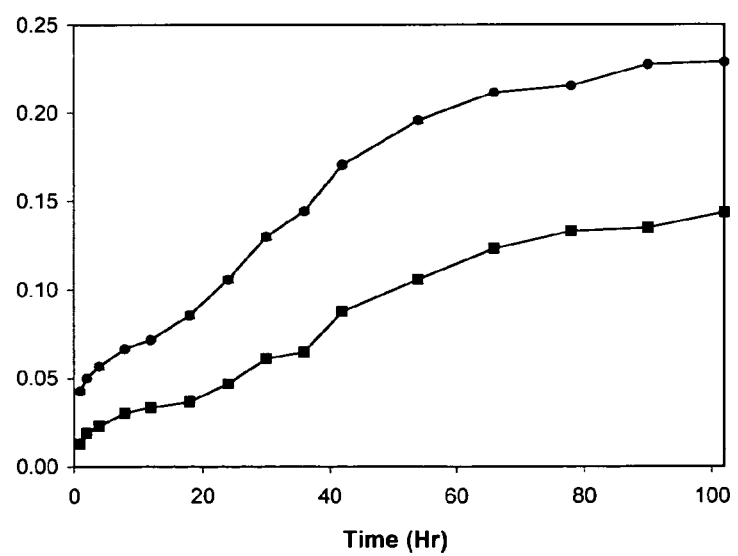
FIG. 7 Plot of solution absorbance at 260 nm v. time for two expanded stents coated with either eight (■) or sixteen (●) bilayers of a polymer 1/DNA film incubated in phosphate buffered saline at 37° C. Error bars are shown but are smaller than the symbols used to represent absorbance values.

Stents coated with polymer 1/DNA multilayered films were incubated in PBS buffer at 37° C. to characterize film erosion and DNA release profiles. FIG. 7 shows a plot of solution absorbance (measured at 260 nm, the absorbance maximum of DNA) versus time for a stent coated with a film eight bilayers thick that was expanded prior to incubation (filled squares; see Materials and Methods for details of incubation procedure). These data demonstrate that following an initial burst that occurs during the first several hours of incubation, absorbance increases in a manner that is approximately linear over a period of up to 65 hours. These data suggest that the release of DNA from the surface of the stent is sustained over a period of 2.5 days under these incubation conditions. On the basis of the final solution absorbance value measured after complete release, it is estimated that the amount of DNA released from this stent coated with eight bilayers of polymer 1 and DNA is 6.1 μg.

FIG. 7 also shows a plot of solution absorbance for a second identical stent coated with 16 bilayers of polymer 1 and DNA and subsequently expanded prior to incubation (FIG. 7, filled circles). With the exception of a larger initial burst, the slope and shape of this release curve are similar to those measured for the stent coated with an eight-bilayer film. These data demonstrate that it is possible to control the total amount of DNA released from a coated stent by increasing the number of layers of DNA deposited during fabrication. It should be noted that the absorbance values measured for the erosion of the 16-bilayer film are not equal to twice the value of the eight-bilayer film, as might be expected if film growth were to proceed in a perfectly linear manner during fabrication. In addition, the stent coated with the 16-bilayer film released a larger amount of DNA, complete release occurred over the same 65 hour time period measured for the release of DNA from the stent coated with an eight-bilayer film. These data are consistent with recent observations for the erosion of multilayered films fabricated from polymer 1 and sodium poly(styrene sulfonate), a model anionic polymer, on planar silicon substrates (J. Zhang, N. J. Fredin, J. F. Janz, B. Sun, D. M. Lynn, Structure/Property Relationships in Erodible Multilayered Films: Influence of Polycation Structure on Erosion Profiles and the Release of Anionic Polyelectrolytes. *Langmuir* 2006, 22, 239-245). In these previous experiments, rates of film erosion and release were also measured to be independent of film thickness or the number of bilayers of material deposited during fabrication.

Figure 8:
FIGS. 8 A and B are scanning electron microscopy images of intravascular stents coated with eight bilayers of a multi-layered polymer 1/DNA film and incubated in PBS buffer at 37° C. for 1.5 hours prior to imaging.
Figure 8:
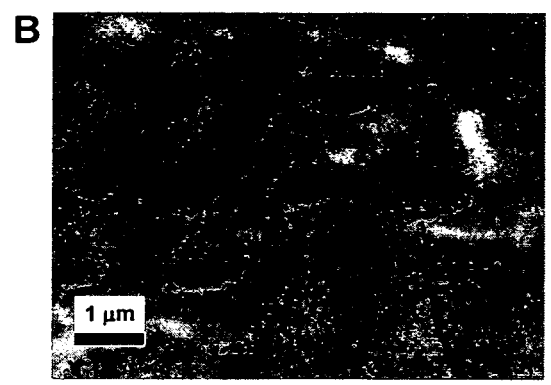

FIG. 8 shows SEM images of a stent coated with eight bilayers of polymer 1 and DNA that was incubated in PBS at 37° C. for 1.5 hours and then dried prior to imaging. These images show clearly that the multilayered film, which was initially smooth and continuous (e.g., FIGS. 5A-F and 6A-D), underwent a structural transformation upon incubation in PBS that resulted in the formation of a topographically complex and textured surface. The morphology of this partially eroded film is consistent with the inventors' previous observations that polymer 1/DNA films fabricated on silicon undergo a transformation that results in the formation of polymer nanoparticles ca. 50 nm to 400 nm in diameter on the surface of coated substrates. The reasons for this behavior and the compositions of these particles are not yet understood. However, because the sizes these particulate structures fall into the range of sizes considered to be suitable for cellular internalization by endocytosis, it is speculated that it may prove possible to design ultrathin polycation/DNA films that act to condense DNA at the surfaces of coated stents and, thus, present or release DNA in a physical form that contributes actively to the transfection of cells (as described below) (C. M. Jewell, J. Zhang, N. J. Fredin, D. M. Lynn, Multilayered Polyelectrolyte Films Promote the Direct and Localized Delivery of DNA to Cells. *J. Control. Release* 2005, 106, 214-223).

Example 6

In Vitro Cell Transfection

Figure 9:
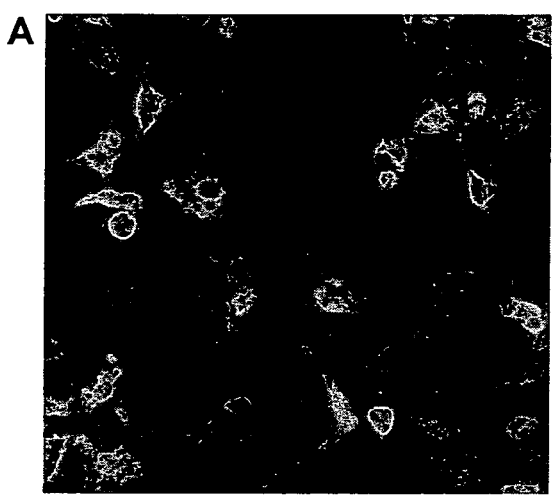
FIGS. 9 A and B are fluorescence microscopy images, A) Fluorescence microscopy image (20×) showing expression of EGFP in COS-7 cells transfected with DNA released from a multilayered polymer 1/DNA film incubated in PBS at 37° C. Transfection was conducted by combining released DNA with a commercially available cationic lipid. B) Series of eighty-eight adjacent low magnification (4×) fluorescence microscopy images showing expression of EGFP in a confluent population of COS-7 cells 48 hours after the introduction of a stent coated with eight bilayers of polymer 1 and DNA (total area shown is approximately 5.7 mm 2; a portion of the expanded stent is shown for comparison). This experiment was conducted without the use of additional transfection agents.
Figure 9:
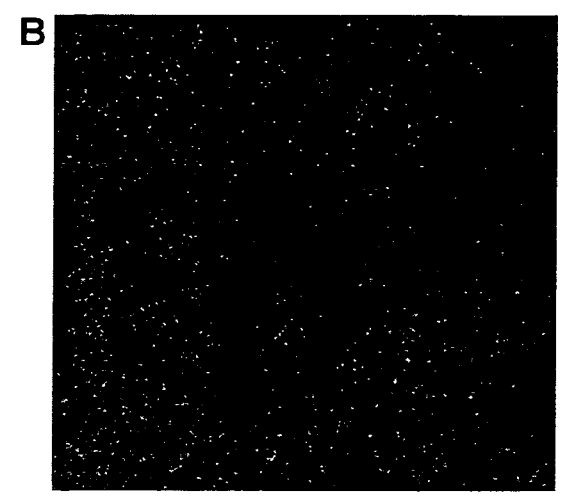

The experiments above suggest that stents coated with multilayered polymer 1/DNA films release plasmid DNA into solution for up to 2.5 days when incubated in physiologically relevant media. Characterization of the DNA released from coated stents using agarose gel electrophoresis demonstrated that the plasmid was released in an open-supercoiled topology, consistent with the results of past studies characterizing the DNA released from polymer 1/DNA films fabricated on silicon and quartz substrates as described in Example 1. Several additional cell-based transfection experiments were performed to characterize the functional integrity of the DNA released from film-coated stents at various time points during the film erosion process. FIG. 9A shows a representative fluorescence microscopy image of COS-7 cells incubated with a commercially available cationic lipid transfection agent and a sample of PBS solution collected during the incubation of a coated stent (see Example 2). These data are consistent with the inventors' results described in Example 1, and demonstrate that the DNA released from the stent surface is released into solution in a form that is capable of yielding high levels of EGFP when combined with a secondary transfection agent.

The inventors also characterized the ability of coated stents to mediate the transfection of cells self-sufficiently, e.g., in the absence of any additional transfection agents. As noted above, the DNA in these multilayered films is juxtaposed intimately with a polyamine, a class of materials used broadly to promote non-viral transfection (D. W. Pack, A. S. Hoffman, S. Pun, P. S. Stayton, Design and development of polymers for gene delivery. *Nature Reviews Drug Discovery* 2005, 4, 581-593). Polymer 1 has been demonstrated to be an effective polymer-based gene delivery agent (D. M. Lynn, R. Langer, Degradable poly(beta-amino esters): Synthesis, characterization, and self-assembly with plasmid DNA. *J Am Chem Soc* 2000, 122, 10761-10768), and the inventors demonstrated, in Example 1, that planar quartz slides coated with polymer 1/DNA films are capable of mediating the localized and contact-mediated transfection of cells. A second set of transfection experiments was conducted in which coated stents were expanded and placed directly into the wells of culture dishes containing cells growing in serum-containing culture medium. FIG. 9B shows a series of adjacent low magnification fluorescence microscopy images of a confluent population of COS-7 cells 48 hours after the introduction of a stent coated with eight bilayers of polymer 1 and DNA (approximate area shown is 5.7 mm 2; a portion of the expanded stent is shown for comparison).

The data in FIG. 9B demonstrate that stents coated with films fabricated from polymer 1 and plasmid DNA are capable of mediating the transfection of cells in the absence of additional transfection agents and in a serum-containing cell culture environment. It is important to note here that the cell transfection observed in this stent-mediated experiment was not localized to portions of the cell population growing in contact with or adjacent to coated stent struts. Rather, observed cells expressing EGFP are distributed equally in all regions of the exposed cell population. The lack of localized transfection in this experiment is likely due to the low percentage of the cell population contacted directly by stent struts and the fact that the stent was not immobilized during incubation. The levels of non-localized transfection observed in the experiment, however, provide support for the view that polymer 1 may act to condense DNA and promote subsequent internalization by cells. For example, control experiments in which identical populations of cells were treated with a bolus of 'naked' plasmid DNA at a concentration of 15 µg resulted in no significant observable transfection after 48 hours (data not shown). The relatively high levels of non-localized transfection shown in FIG. 9B suggest that the DNA released from polymer 1/DNA films may be released in a form that is at least partially condensed by polymer 1 and, therefore, capable of being internalized more effectively by cells. These results show the efficacy of the fabrication of erodible multilayered films using polyamines that condense DNA more effectively and transfect cells as the generic polymer 1 disclosed herein.

In summary, the inventors have disclosed a method for the fabrication of ultrathin, multilayered polyelectrolyte films that permit both the immobilization and controlled release of nucleic acid (e.g., plasmid DNA) from the surfaces of implantable medical devices. This method makes use of an entirely aqueous-based, layer-by-layer method for the assembly of ultrathin films constructed from alternating layers of plasmid DNA and a hydrolytically degradable polyamine. The above experiments demonstrate that films ca. 100 to 130 nm thick that are fabricated conformally onto the topologically complex surfaces, such as those of implantable therapeutic devices, including vascular stents, prosthesis etc. provide ultrathin coatings do not crack, peel, or delaminate from the surface after exposure to mechanical challenges (e.g., expansion) representative of the implantation of such devices. Intravascular stents coated with either eight or 16 bilayers of polymer 1 and a plasmid encoding enhanced green fluorescent protein sustained the release of DNA into solution for up to 2.5 days, and coated stents were capable of mediating the expression of EGFP in a model mammalian cell line without the aid of additional transfection agents.

Materials that permit control over the release of DNA from the surfaces of intravascular stents allow for the development of new approaches for the localized and non-viral delivery of DNA to vascular tissues. The layer-by-layer procedure disclosed herein provides a straightforward mechanism for the fabrication of films constructed from multiple different layers of multiple different DNA constructs (C. M. Jewell, et al., Multilayered Polyelectrolyte Films Promote the Direct and Localized Delivery of DNA to Cells. *J. Control. Release* 2005, 106, 214-223), and shows that various films that permit control over the release of multiple different genes from stent surfaces will be effective in modulating the release of various therapeutics contained in the thin film. Further, the internal structures of these ultrathin materials, in which DNA is juxtaposed intimately with cationic polymer, provide a platform upon which to design films that act to promote the uptake and expression of DNA. Increasing the hydrophobicity of the degradable polyamine used to fabricate these films will allow the fabrication of ultrathin erodible polyelectrolyte assemblies that sustain the release of DNA for longer periods of time (J. Zhang, et al., Structure/Property Relationships in Erodible Multilayered Films: Influence of Polycation Structure on Erosion Profiles and the Release of Anionic Polyelectrolytes. *Langmuir* 2006, 22, 239-245; J. Zhang, N. J. Fredin, D. M. Lynn, Erosion of Multilayered Films Fabricated from Degradable Polyamines: Characterization and Evidence in Support of a Mechanism that Involves Polymer Hydrolysis. *Journal of Polymer Science—Part A: Polymer Chemistry* 2006, 44, in press). Finally, in comparison to conventional methods reported for the encapsulation of DNA in polymeric stent coatings, the methods introduced here do not require the use of organic solvents and they reduce dramatically the amount of polymer required to immobilize and release DNA at the surface. The ultrathin films reported here further development, contribute to the development of localized gene-based approaches to the treatment of cardiovascular diseases and related conditions.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments. All publications, patents and patent applications cited herein are hereby incorporated by reference in their entirety for all purposes.

What is claimed is:

1. An implantable medical device capable of localized delivery of nucleic acid encoding a polypeptide to a cell, comprising:
   (a) an implantable medical device; and
   (b) a polyelectrolyte assembly coating a surface of the medical device wherein said polyelectrolyte assembly comprises a multilayer film having a thickness of at least 100 nm,
   wherein said multilayer film comprises at least two bilayers, wherein each bilayer comprises a positively charged polycation first layer in contact with a negatively charged nucleic acid second layer, wherein the positively charged polycation layer alternates with the negatively charged nucleic acid layer, said alternated polycation and nucleic acid layers deposited on the surface of the medical device using a layer-by-layer fabrication procedure,
   wherein said nucleic acid comprises an expression vector comprising one or more regulatory sequences and a nucleotide sequence encoding a polypeptide, and said nucleic acid is released by said polyelectrolyte assembly and delivered to said cell without use of any additional transfection reagents resulting in expression of said polypeptide by said cell, when said cell is in contact or near the coated surface of the medical device, and
   wherein said polycation is a polymer selected from the group consisting of poly(betaaminoester)s, polyethyleneimines, polyphosphoesters and dynamic charge state cationic polymers having a polymeric backbone formed from monomeric units, and one or more removable functional groups attached to the polymeric backbone through one or more labile linkages wherein the overall positive charge of the cationic polymer decreases when one or more of the removable functional groups is removed from the polymeric backbone.

2. The implantable medical device of claim 1 wherein said polycation is a hydrolytically or enzymatically degradable polycation polymer.

3. The implantable medical device of claim 2 wherein said hydrolytically or enzymatically degradable polycation is selected from the group consisting of poly(betaaminoester)s.

4. The implantable medical device of claim 1, wherein the multilayer film comprises at least four bilayers.

5. The implantable medical device of claim 1, wherein the nucleic acid includes at least two nucleic acids that differ by nucleic acid sequence.

6. The implantable medical device of claim 1, wherein the nucleic acid encodes a polypeptide selected from the group consisting of endostatin, angiostatin, an inhibitor of vasoactive endothelial growth factor (VEGF), an inhibitor of a signal protein in a signaling cascade of vascular endothelial growth factor, and inhibitor of basic fibroblast growth factor (bFGF), an inhibitor of a signal protein in a signaling cascade of bFGF and combinations thereof.

7. The implantable medical device of claim 1, wherein the device is selected from the group consisting of a stent, a pacemaker, a defibrillator, an artificial joint, a prosthesis, a neurostimulator, a ventricular assist device, congestive heart failure device, an indwelling catheter, an insulin pump, an incontinence device, a cochlear device, and an embolic filter.

8. A method of delivering to a cell a nucleic acid comprising an expression vector comprising one or more regulatory sequences and a nucleotide sequence encoding a polypeptide, said method comprising:
   a) placing a polyelectrolyte assembly in contact with or near a cell, wherein said polyelectrolyte assembly comprises a multilayer film having a thickness of at least 100 nm,
   wherein said multilayer film comprises at least two bilayers, wherein each bilayer comprises a positively charged polycation first layer in contact with a negatively charged nucleic acid second layer, wherein the positively charged polycation layer alternates with the negatively charged nucleic acid layer, said alternated polycation and nucleic acid layers in the multilayer film fabricated by layer-by-layer deposition of said polycation and nucleic acid,
   b) locally delivering said nucleic acid into the cell, wherein said cell is in contact with or near the polyelectrolyte assembly without use of any additional transfection reagents, and
   c) expressing in said cell the polypeptide encoded by said nucleotide sequence,
   wherein said polycation is a polymer selected from the group consisting of poly(betaaminoester)s, polyethyleneimines, polyphosphoesters and dynamic charge state cationic polymers having a polymeric backbone formed from monomeric units, and one or more removable functional groups attached to the polymeric backbone through one or more labile linkages wherein the overall positive charge of the cationic polymer decreases when one or more of the removable functional groups is removed from the polymeric backbone.

9. The method according to claim 8 wherein said polycation is a hydrolytically or enzymatically degradable polycation polymer.

10. The method according to claim 9 wherein said hydrolytically or enzymatically degradable polycation is selected from the group consisting of poly(betaaminoester)s.

11. The method according to claim 9 wherein the multilayer film comprises at least four bilayers.

12. The method according to claim 8 wherein said polyelectrolyte assembly includes at least two nucleic acids that differ by nucleotide sequence, the two nucleic acids residing in different bilayers to facilitate sequential delivery of said two nucleic acids into the cell.

13. The method according to claim 8 wherein said nucleic acid is deoxyribonucleic acid (DNA).

14. The method according to claim 8 wherein said method is carried out in the presence of cell culture medium.

15. The method according to claim 8 wherein said cell is contained within a living tissue.

16. The method according to claim 8 wherein said polyelectrolyte assembly is provided on a surface of an implantable medical device.

17. A method of providing an implantable medical device capable of localized delivery of a nucleic acid, said nucleic acid comprising an expression vector encoding a polypeptide, said method comprising:
   depositing alternating layers of a nucleic acid and a polycation on a surface of the implantable medical device to provide a polyelectrolyte assembly coating at least a portion of the surface of said implantable medical device, the polyelectrolyte assembly comprising a multilayer film having a thickness of at least 100 nm,
   wherein said multilayer film comprises at least four bilayers, wherein each bilayer comprises a positively charged polycation first layer in contact with a negatively charged nucleic acid second layer, said alternated polycation and nucleic acid layers in the multilayer film fabricated by layer-by-layer deposition of said polycation and nucleic acid, and wherein said nucleic acid is released by said polyelectrolyte assembly and delivered to said cell without the use of any additional transfection reagents, resulting in expression in said cell of the polypeptide encoded by said nucleotide sequence,
   wherein said polycation is a polymer selected from the group consisting of poly(betaaminoester)s, polyethyleneimines, polyphosphoesters and dynamic charge state cationic polymers having a polymeric backbone formed from monomeric units, and one or more removable functional groups attached to the polymeric backbone through one or more labile linkages wherein the overall positive charge of the cationic polymer decreases when one or more of the removable functional groups is removed from the polymeric backbone.

18. The method according to claim 17 wherein said polycation is a hydrolytically or enzymatically degradable polycation polymer.

19. The method according to claim 18 wherein said hydrolytically or enzymatically degradable polycation is selected from the group consisting of poly(beta-amino ester)s.

20. The method according to claim 17 wherein said nucleic acid encodes a polypeptide selected from the group consisting of endostatin, angiostatin, an inhibitor of vasoactive endothelial growth factor (VEGF), an inhibitor of a signal protein in a signaling cascade of vascular endothelial growth factor, and inhibitor of basic fibroblast growth factor (bFGF), an inhibitor of a signal protein in a signaling cascade of bFGF and combinations thereof.

21. The method according to claim 17 wherein the implantable device is selected from the group consisting of a stent, a pacemaker, a defibrillator, an artificial joint, a prosthesis, a neurostimulator, a ventricular assist device, congestive heart failure device, an indwelling catheter, an insulin pump, an incontinence device, a cochlear device, and an embolic filter.

* * * * *